US010463495B2

(12) United States Patent
Rogers et al.

(10) Patent No.: US 10,463,495 B2
(45) Date of Patent: Nov. 5, 2019

(54) ENCIRCLING IMPLANT DELIVERY SYSTEMS AND METHODS

(71) Applicant: The United States of America, as represented by the Secretary, Department of Health and Human Services, Bethesda, MD (US)

(72) Inventors: Toby Rogers, Washington, DC (US); Robert J. Lederman, Chevy Chase, MD (US); Merdim Sonmez, Bethesda, MD (US); Dominique N. Franson, Gaithersburg, MD (US); Ozgur Kocaturk, Rockville, MD (US)

(73) Assignee: The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 895 days.

(21) Appl. No.: 14/898,020

(22) PCT Filed: Jun. 3, 2014

(86) PCT No.: PCT/US2014/040716
§ 371 (c)(1),
(2) Date: Dec. 11, 2015

(87) PCT Pub. No.: WO2014/200764
PCT Pub. Date: Dec. 18, 2014

(65) Prior Publication Data
US 2016/0120647 A1    May 5, 2016

Related U.S. Application Data

(60) Provisional application No. 61/834,357, filed on Jun. 12, 2013.

(51) Int. Cl.
*A61F 2/24* (2006.01)
*A61B 17/221* (2006.01)
*A61B 17/00* (2006.01)

(52) U.S. Cl.
CPC ...... *A61F 2/2481* (2013.01); *A61B 17/00234* (2013.01); *A61B 17/221* (2013.01);
(Continued)

(58) Field of Classification Search
CPC .......... A61F 2/2481; A61F 2002/2484; A61B 17/00234; A61B 17/221;
(Continued)

(56) References Cited

U.S. PATENT DOCUMENTS 5,281,238 A  *  1/1994  Chin ................ A61B 17/06166
                                                     606/113
2008/0243183 A1 * 10/2008 Miller ............. A61B 17/12013
                                                     606/228

(Continued)

OTHER PUBLICATIONS

International Search Report and Written Opinion for related International Application No. PCT/US2014/040716, dated Sep. 22, 2014, 12 pages.

*Primary Examiner* — Katherine M Rodjom
(74) *Attorney, Agent, or Firm* — Klarquist Sparkman, LLP

(57) ABSTRACT

Delivery devices for delivering encircling implants can include two separate limbs that are held together at a distal articulation by the implant being delivered. The implant can comprise a suture and/or a braided tube. The implant can extend through or over the limbs. The implant and at least a distal portion of the limbs can be compressible into a delivery shape that allows for advancement through the lumen of a delivery catheter. When the distal portion of the limbs move out of the delivery catheter, the limbs and implant can resiliently assume a loop shape that is comple-
(Continued)

mentary to a shape of a target around which the encircling implant is to be placed. The limbs are then retracted from along the implant to leave the implant in the desired delivery position. The delivery device can be used to place encircling implants around the heart or other targets, and the implant can be tightened to exert compressive force on the target.

36 Claims, 17 Drawing Sheets

(52) U.S. Cl.
CPC ............... *A61B 2017/00243* (2013.01); *A61B 2017/00278* (2013.01); *A61B 2017/00292* (2013.01); *A61B 2017/00358* (2013.01); *A61B 2017/2212* (2013.01); *A61F 2002/2484* (2013.01)

(58) Field of Classification Search
CPC .......... A61B 2017/00243; A61B 2017/00278; A61B 2017/00292; A61B 2017/00358; A61B 2017/2212
See application file for complete search history.

(56) References Cited

U.S. PATENT DOCUMENTS

| 2010/0081867 A1 | 4/2010 | Fishler et al. |
| 2011/0015478 A1 | 1/2011 | Vanden Hoek et al. |

\* cited by examiner

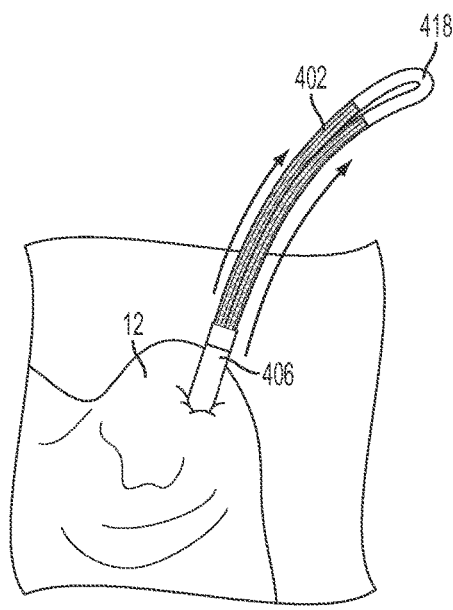
FIG. 15
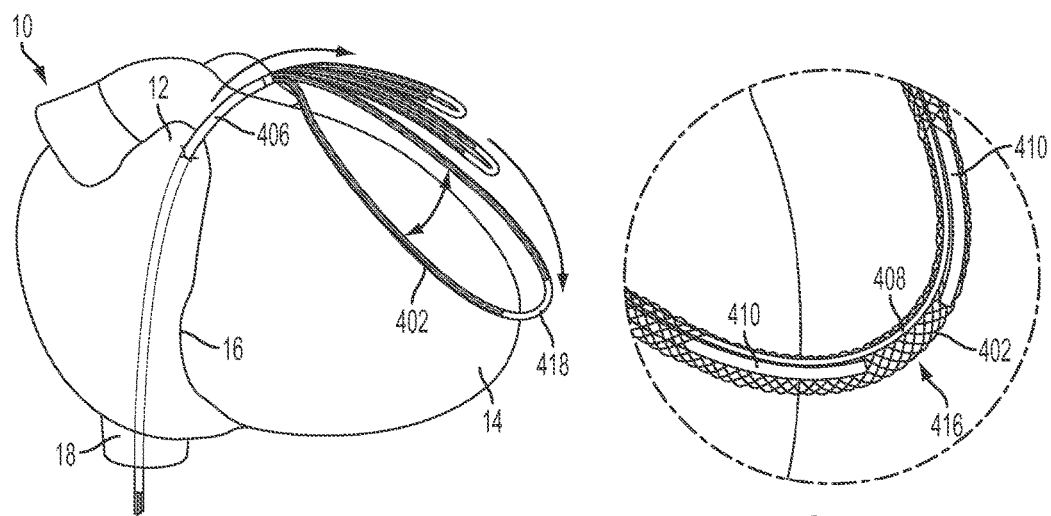
FIG. 16
FIG. 17

FIG. 22A 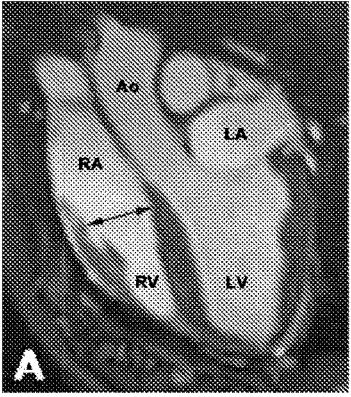 FIG. 22B
FIG. 22C 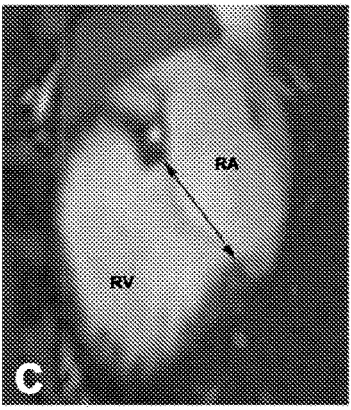 FIG. 22D

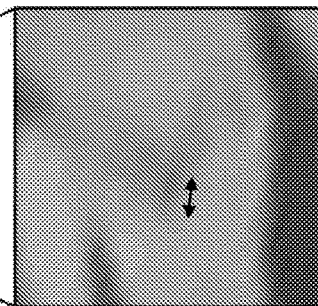

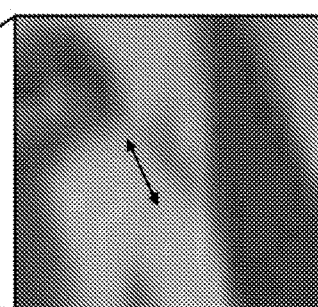

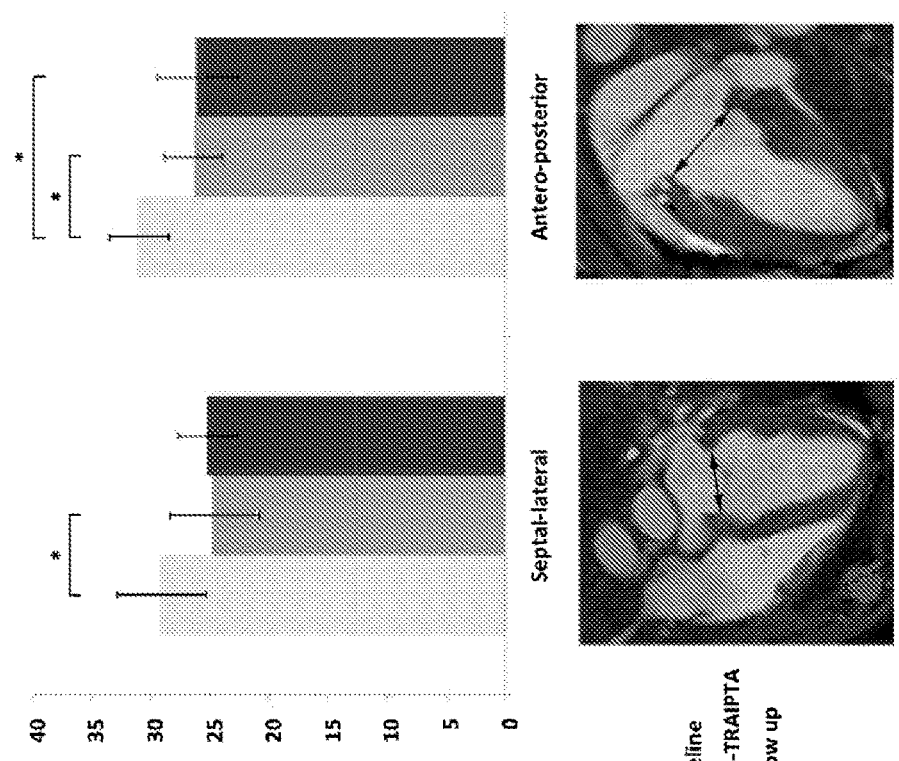
FIG. 23B
FIG. 23A
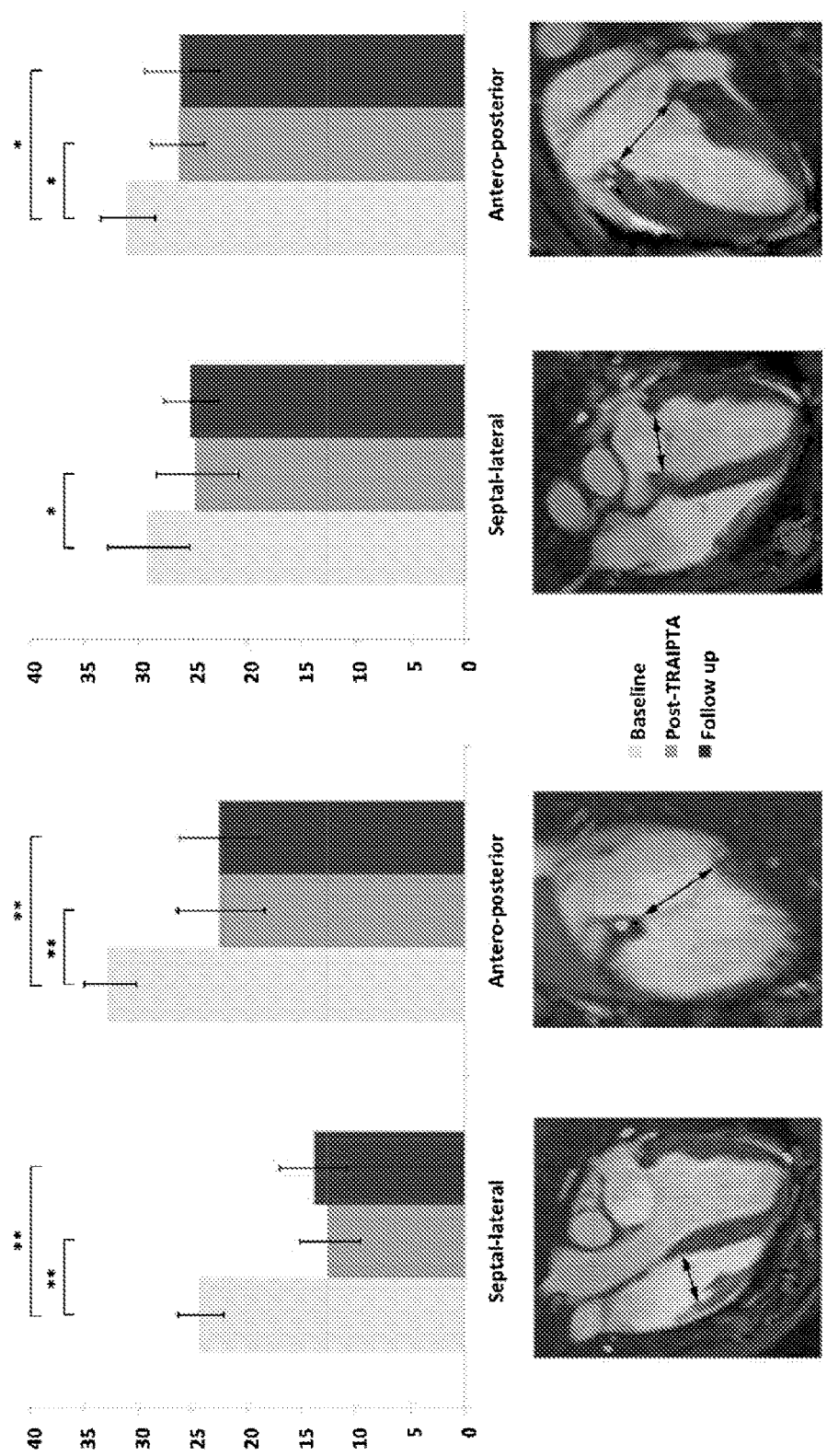

FIG. 25A
FIG. 25B
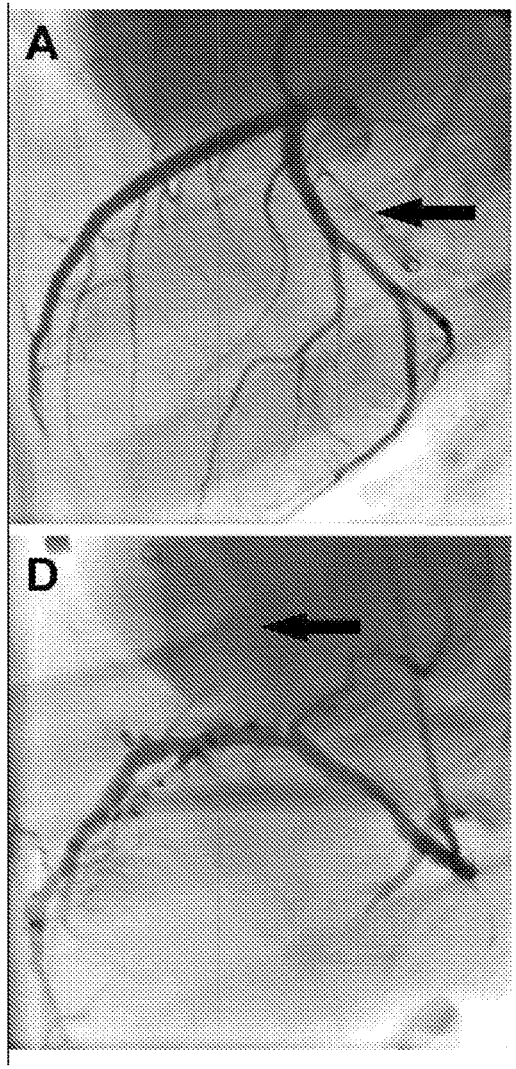
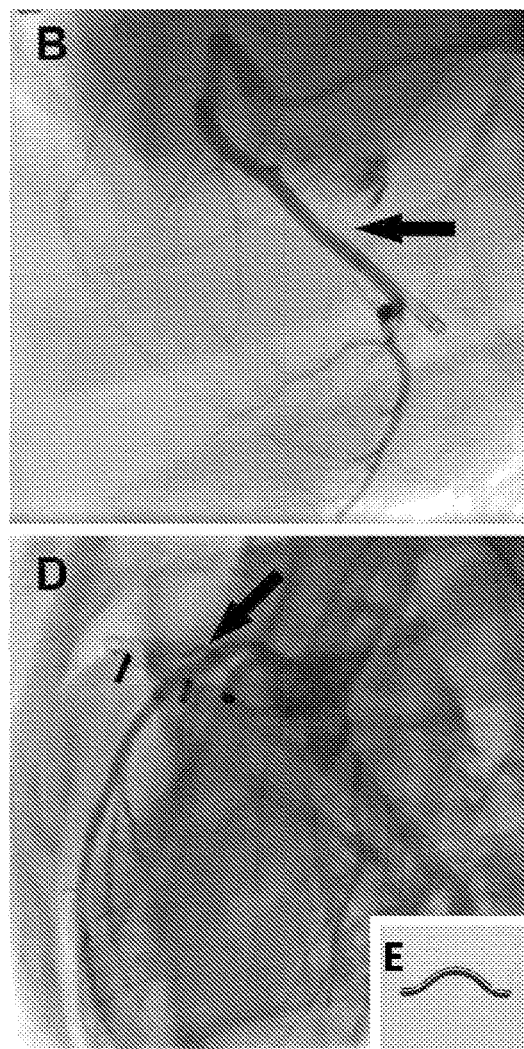
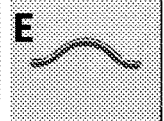
FIG. 25C
FIG. 25D
FIG. 25E

ENCIRCLING IMPLANT DELIVERY SYSTEMS AND METHODS

CROSS REFERENCE TO RELATED APPLICATIONS

This is the U.S. National Stage of International Application No. PCT/US2014/040716, filed Jun. 3, 2014, which was published in English under PCT Article 21(2), and which claims the benefit of U.S. Provisional Patent Application No. 61/834,357, filed Jun. 12, 2013. The provisional application is incorporated by reference herein in its entirety.

RELATED APPLICATION

This application claims priority to U.S. Provisional Application No. 61/834,357, filed Jun. 12, 2013, which is incorporated by reference in its entirety.

FIELD

This disclosure relates to devices and methods for delivering an encircling implant around an anatomic structure in the body.

BACKGROUND

Transcatheter procedures have enabled minimally invasive procedures that reduce morbidity, improve recovery time, and permit interventions to be performed on subjects who are not otherwise candidates for surgery. For example, transcatheter cardiovascular procedures have been widely used in recent years to perform angioplasty, place coronary artery stents, replace diseased or injured heart valves, and treat heart valve dysfunction by compressing the myocardial wall overlying the valve. However, advances in transcatheter procedures have been accompanied by challenges in developing technologies for remotely manipulating and modifying tissue and other objects within the body through the catheters.

One such challenge has been developing technology utilizing transcatheter procedures for encircling a target structure within the body with a continuous loop, such as a suture, such that the loop can be remotely tightened to compress the target structure around which the loop is positioned.

SUMMARY

Disclosed herein are delivery systems for delivering encircling implants through a catheter for placement around anatomical targets, such the heart or other organs. In some embodiments, the delivery systems can include two limbs that are held together at a distal articulation tip by the implant being delivered. The limbs can have separate proximal portions running through the catheter, or can be joined to form a single proximal portion running through the catheter. The implant can comprise a suture and/or a braided tube, for example, that is placed around the target structure for applying compressive force on the target structure. The implant can extend through or around the limbs of the delivery device during delivery. For example, in some embodiments an encircling suture implant runs through lumens of the limbs, while in other embodiments an encircling tubular implant extends over the limbs. The implant and at least a distal portion of the limbs can be compressible into a delivery shape that allows for advancement through the lumen of a delivery catheter. When the distal portion of the limbs move out of the delivery catheter, the limbs can resiliently assume a predetermined loop shape that is complementary to a shape of a target around which the encircling implant is to be placed. The limbs can cause the implant to assume the similar loop shape. The limbs are then separately retracted from within or around the implant to leave the implant in the desired delivery position. In some embodiments, the implant can then be tightened to exert compressive force on the target. In embodiments having a tubular implant, a separate suture can run through the implant that can be tightened to apply compressive force to the implant and secure the implant around the target structure.

Some disclosed delivery devices for delivering a tubular implant include a guide having two resiliently deformable arms extending distally from a common proximal trunk and/or proximal portion that extends through the catheter and allows both arms to be retracted from within the tubular implant at the same time around opposite sides of the target structure. The tubular implant is folded in half during delivery with one half over one arm and the other half over the other arm, and with a fold or crease at a distal end bridging the gap between the distal ends of the two arms. The tubular implant can itself be resiliently deformable to help it unfold after being advanced out of the delivery catheter and assume the desired loop shape. The tubular implant can comprise a braided or woven material that allows the tubular implant to lengthen and shorten. The implant can comprise nitinol strands, for example, that form a braided tube that is resiliently deformable in the longitudinal shortening and lengthening directions, as well as in a manner that allows it to unfold and assume the desired loop shape. A suture or other cord can run through the braided tubular implant that can be tightened by pulling on a proximal end of the suture that extends through the delivery catheter. For example, the suture can include a slip knot or locking device adjacent to the two ends of the tubular implant that allows the looped portion of the suture passing through the implant to be adjusted in circumference. As the circumference of the suture loop is reduced, the tubular implant can tighten around the target and can reduce in length to prevent the implant from buckling or kinking. Further, the presence of the tubular material between the suture and the target tissue can prevent damage from the suture cutting into the tissue.

Some disclosed delivery devices for delivering an encircling suture implant include two separate hollow limbs that are held together at a distal articulation tip by the suture that is to be delivered. The suture extends through the hollow limbs which slide along the suture. At least a distal portion of the limbs is compressible into a delivery shape that allows the limbs to be advanced through the lumen of a delivery catheter. As the distal portions of the limbs move out of the delivery catheter, the limbs cooperatively assume a loop shape that is complementary to the shape of a target around which the encircling suture is to be placed. The two limbs are then separately slid off opposite ends of the suture to leave only the suture in the desired delivery position while maintaining desired (for example constant) suture tension and position on the encircled structure. The delivery device can be used to place encircling sutures around an anatomic structure such as the heart or other organs, and the suture can be tightened to exert compressive force on the anatomic structure.

In some embodiments, a delivery device can include separate first and second delivery limbs linked at an articulation by a continuous flexible suture that is to be delivered and which extends through or around the first and second limbs to maintain the first and second delivery limbs together in an articulating relationship at an articulation tip. Each limb may include a proximal limb portion and a distal limb portion, and at least the distal limb portion of each limb is made of a material that is resiliently deformable into the delivery shape. When not deformed into the delivery shape the distal limb portions are configured to cooperatively form with a contralateral limb a loop that can be placed circumferentially around the portion of the target structure.

In some examples, the target structure is an anatomic or implanted structure in the body of a subject, for instance a target structure having a base portion connected to the body and a free portion over and around which the loop can be passed. In other examples, the target structure is a body organ, a portion of a body organ, or a surgically implanted device. Specific examples of target structures include a heart or atrial appendage, a cecal appendix, a gallbladder, a neoplasm, a uterus, a hemorrhoid, an uvula, an aneurysm, a transected blood vessel or other transected, folded or looped lumen, an intraocular crystalline lens or implanted intraocular lens or lens haptic, a urinary bladder, a kidney, a prostate or a foreign body. Targeted neoplasms particularly include examples such as polyploid or sessile neoplasms, for example colonic or nasal polyps.

The distal limb portions of the device can be cooperatively biased to assume a loop shape and size substantially complementary to the portion of the target structure around which the loop is to be circumferentially placed. The proximal limb portions of the first and second delivery limbs may be substantially parallel to one another in the delivery shape, and the distal limb portions may be substantially parallel to one another in the delivery shape. For example, the proximal and distal limb portions can be constrainable into the delivery shape by a lumen within a flexible delivery catheter though which the encircling suture is to be delivered to the target structure in the body. Delivery catheters can have a distal end for initial introduction into the body and an open proximal end into which the delivery device is introduced and through which it may be controlled. The catheter may optionally have a tip that is capable of perforating tissue, or may be incorporated into or associated with a device (such as an endoscope) that has such capability. The catheter may be rigid or flexible or steerable (for example when incorporated into or otherwise associated with an endoscope).

In some embodiments, the limbs are flexible to conform to the shape of the lumen within the flexible delivery catheter, for example with the limbs parallel to one another within the confined space within the lumen. The proximal limb portions are able to maintain a substantially parallel relationship when only a distal portion of the proximal limb portions extend from the lumen, and the proximal limb portions may be connected together in at least one location to constrain their relative rotation and/or maintain them substantially parallel.

The suture has first and second terminal ends, and the suture may extend continuously through the delivery limbs within the percutaneous delivery device with the first and second terminal ends of the suture extending from an open proximal tip of the proximal limbs and/or the open proximal end of the delivery catheter. In another embodiment, the terminal ends of the suture emerge through an intermediate opening along each of the first and second delivery limbs (a "monorail" embodiment). The suture may be of any material that is sufficiently flexible and strong, such as fiber or wire, and can perform the intended function of the suture, such as tightening around and securing the target structure. In particular embodiments, the suture is capable of compressing the target structure, for example as a cerclage. The first and second delivery limbs are capable of being withdrawn from the suture, the catheter, and/or the body once the encircling suture is delivered around the target structure thereby leaving only the exposed suture encircling the target structure.

The loop is cooperatively formed by the distal limb portions when they are not deformed into the delivery shape, each distal limb portion forming substantially half of the loop, or each distal limb is symmetric or asymmetric with respect to its contralateral limb, or one or both distal limbs is semilunar, semi-ovoid, semi-circular, or substantially C-shaped, J-shaped, L-shaped, S-shaped, V-shaped or U-shaped. In some embodiments, the loop is substantially circular or cordiform and each distal limb portion forms a substantially semi-lunar or semi-cordiform shape joined at the articulation tip. The flexible distal limb portions cooperatively from geometric shapes, and the shape formed by each limb portion may be co-planar or not co-planar with the contralateral limb portion. The loop may extend at a predetermined angle with respect to a longitudinal axis of the proximal limb portion, for example by folding back toward the proximal limb portion.

Methods of use are also disclosed, such as methods of using the device to deliver an encircling suture around a target structure in a body through an elongated delivery catheter having a lumen, a proximal control end and a distal end. The delivery limbs are advanced through the catheter, articulated tip first, with the proximal and distal limb portions conforming to the delivery shape within the delivery catheter with the proximal and distal limb portions substantially conforming to the shape of the lumen of the delivery catheter. As the delivery limbs are further advanced the distal limb portions emerge from the lumen at the distal end of the delivery catheter, and the distal limb portions form the loop while at least a portion of the proximal limb portions are retained within the delivery catheter, for example in a substantially parallel relationship. The loop is then placed around the target structure to encircle it. The first and second delivery limbs may be individually or cooperatively moved to adjust the orientation of the loop with respect to the delivery catheter and the target structure to navigate or deliver the loop around the target. The first and second delivery limbs are then withdrawn over the suture and retracted into the delivery catheter to leave the now-exposed suture positioned and secured around the target structure. The suture can then be tightened around the target structure, for example to compress it. The delivery catheter can then be withdrawn from the suture delivery site or withdrawn entirely from the body.

The method can include introducing the catheter to the delivery site by a variety of methods. For example, the distal end of the delivery catheter can be introduced percutaneously or intraluminally into the body and the distal end of the delivery catheter then advanced to the target structure within the body. In some embodiments, the delivery catheter is inserted percutaneously through an introducer sheath into the body and advanced intravascularly through the inferior vena cava until the distal end of the delivery catheter penetrates the wall of the heart. The delivery limbs are then advanced out of the distal end of the delivery catheter until the distal delivery limbs form a loop that substantially conforms to the shape of a circumference of the heart. In a particular disclosed example, the loop assumes a pre-configured angle with respect to the proximal portions of the limbs, and the loop is advanced around the apex of the heart within the pericardial space, if the pericardium is intact, until the loop encircles the heart. The delivery limbs are then withdrawn proximally into the catheter to expose the suture which encircles the heart, and the suture is tightened by exerting tension on the terminal ends of the suture, for example to improve the function of a heart valve within the heart.

In some examples of the method, the distal end of the delivery catheter penetrates the heart through an atrial appendage, and the loop is configured to substantially conform to a circumference of a targeted atrial appendage of the heart. The loop is advanced around the atrial appendage within the pericardial space, if present, until the loop encircles the targeted atrial appendage. Then the delivery limbs are withdrawn proximally into the catheter to expose the suture encircling the targeted atrial appendage and the suture is tightened by exerting tension on the terminal ends of the suture to exclude the targeted atrial appendage. Alternatively, the distal end of the delivery catheter approaches the heart by a trans-thoracic or sub-xiphoid path and the loop is advanced around the atrial appendage until the loop encircles the atrial appendage. Then the delivery limbs are withdrawn proximally into the catheter to expose the suture which encircles the atrial appendage and the suture is tightened by exerting tension on the terminal ends of the suture to tighten the suture and exclude the atrial appendage.

In alternative embodiments of the method, the distal end of the delivery catheter is inserted intraluminally into a body lumen or cavity and advanced to the target structure, for example through or otherwise in association with a laparoscope or bronchoscope. In some embodiments the body lumen is a gastrointestinal, genitourinary, vascular or respiratory lumen. Intraluminal embodiments may be introduced through an external body orifice (such as the mouth, nose or anus) instead of transcutaneously. However, a body cavity can also be entered through the skin, for example by insertion of a laparoscope though the abdominal wall into the peritoneum. Examples of other cavities into which the device may be introduced include the peritoneum, an anterior or posterior chamber of the eye, a gastrointestinal cavity, the pelvic cavity, a thoracic cavity, a uterine cavity, a urinary bladder, or a ventricle of the brain.

The device can be configured and used to perform a variety of transcatheter procedures such as the cardiovascular procedures discussed above. Other uses include grasping, retrieval, and/or repositioning of foreign bodies such as surgically implanted devices. The device can be used to introduce a protection or compression member to the target structure by advancing the compression member over the suture to a desired position with respect to the target structure. For example, when the target structure is the heart, and the compression device is advanced over the suture to a position on an external wall of the myocardium to exert pressure on its external wall to change a shape and function of a valve of the heart, such as a mitral or tricuspid valve. Alternatively, a protection device is advanced over the suture to a position on an external wall of the myocardium to bridge a coronary artery and avoid compression of the coronary artery when the suture is tightened around the heart. In yet other applications, the target structure is the right ventricular outflow tract or main pulmonary artery.

Methods are also disclosed for making a device for transcatheter delivery of a continuous flexible encircling suture around a circumference of a target structure within a body of a subject. First and second delivery limbs are linked at an articulation by placing the suture through or around the first and second limbs to maintain the first and second delivery limbs together in an articulating relationship at an articulation tip. Each limb includes a proximal and distal limb portion. Each proximal limb portion has a delivery shape for advancement through a lumen, and each distal limb portion is resiliently deformable into the delivery shape. However the distal limb portion forms a portion of a loop when not deformed into the delivery shape, and the two distal limbs in the delivery position cooperatively form a loop that can be placed circumferentially around the target structure. The articulation tip may be introduced into a catheter lumen of a flexible catheter, and advanced distally within the catheter lumen until the proximal and distal limb portions are both compressed into a substantially linear delivery shape for advancement through the catheter to the target location.

The foregoing and other features and advantages of the invention will become more apparent from the following detailed description of a several embodiments which proceeds with reference to the accompanying figures. This summary of the description is intended as a summary of multiple specific embodiments of the device and method for the convenience of the reader, and are not to be construed as limitations of the claims or delineation of any essential elements.

BRIEF DESCRIPTION OF THE FIGURES

FIG. 15 is an enlarged view of the atrial appendage illustrating the initial deployment of the delivery system of FIG. 14 through the right atrial appendage into the pericardial space.

FIGS. 16-18 show the heart and illustrate deployment of the rigid loop and implant from the delivery catheter such that they assume their preconfigured and unconstrained loop configuration, and advancement of the loop over the apex of the heart to encircle the heart. The preformed shape of the loop allows it to surround the target structure (in this case the heart) and further be manipulated to its targeted position (in this case the atrioventricular groove). FIG. 17 shows an enlarged portion of the loop, showing the rigid arms and suture within the tubular implant.

FIGS. 22A-F are MRI images showing views of the heart anatomy before and after an encircling implant is applied around the heart.

FIGS. 23A and 23B illustrates geometric changes in the heart resulting from placement of the encircling implant.

FIG. 25A-D shows coronary arteries and coronary sinus angiography following annuloplasty with an encircling suture. FIG. 25E shows an exemplary protective member that can be placed along an encircling implant to bridge over a vessel or other sensitive part of the target structure.

DETAILED DESCRIPTION

Explanation of Terms and Embodiments

Figure 1:
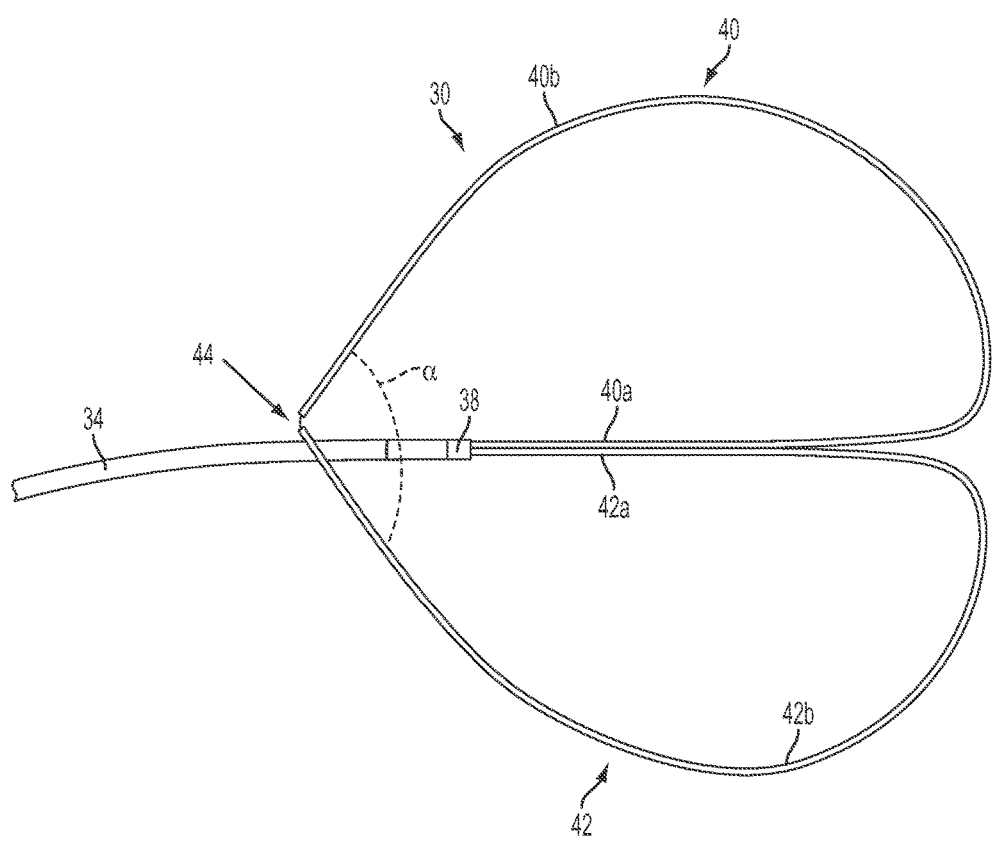
FIG. 1 is a view of the hollow limbs of the delivery device extending from the open distal tip of a delivery catheter, with the distal limbs assuming a preformed configuration that forms a loop for placement around a target structure.

Unless otherwise noted, technical terms are used according to conventional usage. In order to facilitate review of the various embodiments of the disclosure, the following explanation of terms is provided:

"Annuloplasty element" refers to a device that induces reshaping of an annulus of the heart to repair valvular insufficiency. Such devices include those that are placed in the atrioventricular groove of the heart and exert their action by compressive forces on the annulus, for example by expansion of a resilient annuloplasty element, or placement of the annuloplasty element under tension, as in cerclage annuloplasty.

A "catheter" is a thin tube typically made of medical grade materials that can be inserted into the body to diagnose or treat disease or perform a medical/surgical procedure. Catheters can be modified to tailor them for cardiovascular, urological, gastrointestinal, neurovascular, ophthalmic and other applications. Catheters can be inserted into any body cavity or lumen, for example over a guide wire or through an introducer sheath. Some catheters may be made of a flexible material and/or have multiple lumens through which different instruments or therapeutic agents can be introduced. The catheter can function independently of or be incorporated into other instruments, such as a flexible endoscope. Endoscopic devices include endoscopes for introduction into the gastrointestinal tract (EGD, enteroscopy, colonoscopy, sigmoidoscopy), respiratory tract (rhinoscopy, bronchoscopy), ear (otoscopy), urinary tract, female reproductive system, abdominal or pelvic cavity (laparoscopy), interior of a joint (arthroscopy), organs of the chest (thoracoscopy and mediastinoscopy), the amnion (amnioscopy), fetus (fetoscopy), epidural space (epiduroscopy), and the eye (as in retinoscopy). The catheter may be inserted separately along with the endoscope, for example by being attached to the endoscope, or be incorporated into the endoscope as a separate lumen within the flexible tube that also contains the endoscope.

The term "compression member" refers to an element that is designed to cooperate with the tensioning element to apply a desired force to an area along the path of the tensioning element. The compression member may be designed to provide a greater force to the area than would be applied by the tensioning element alone.

The term "comprises" means "includes without limitation." Thus, "comprising A and B" means "including A and B" without excluding additional elements.

"Contralateral" refers to a corresponding part on an opposite side. In anatomy, the terms "ipsilateral" and "contralateral" typically refer to opposing portions of a corporeal lumen having symmetric right and left sides.

A "device for tricuspid valve annuloplasty" refers to a device that induces reshaping of an annulus of the heart's tricuspid valve to repair valvular insufficiency. Such devices include those that are placed in contact with the annulus of the triscuspid valve, and include those that exert their action by compressive forces on the annulus, such as by placing a flexible annuloplasty member under tension, as in cerclage annuloplasty.

The terms "distal" and "distally" refer to a location or direction that is, or a portion of a device that when implanted (for example placed within a blood vessel) is further downstream or farther away from the point of insertion. The terms "proximal" and "proximally" refer to a location or direction that is, or a portion of a device that when implanted, or placed within the blood vessel, is further upstream or closest to the point of insertion.

A "flexible member" refers to an element that is sufficiently flexible to be introduced into the body, generally as or through a catheter, and manipulated along a desired path within the body, such as in and around the patient's heart. One example of such a flexible member is a "guide wire" of a conventional catheter. The guide wire also can deliver energy to augment its ability to penetrate tissue, for example by puncturing it, delivering radiofrequency ablative energy or by delivering laser ablative energy.

"Guide wire" refers to a simple guide wire, a stiffened guide wire, or a steerable guide-wire catheter that is capable of puncturing and/or penetrating tissue. The guide-wire also can deliver energy to augment its ability to penetrate tissue, for example by puncturing it, delivering radiofrequency ablative energy or by delivering laser ablative energy. These are examples of a "penetrating device," which is a device capable of penetrating heart tissue, such as the myocardium.

A "mitral valve cerclage annuloplasty" refers to an annuloplasty procedure in which a tensioning element is placed around the heart, for example through or over at least a portion and preferably all of the coronary sinus, so that the circumferential tension is delivered around the mitral valve annulus and so that a tensioning element can be placed under selective degrees of tension to perform the annuloplasty. An example of cerclage annuloplasty is disclosed in U.S. Patent Publication No. 2005/0216039, which is incorporated herein by reference. However, mitral valve cerclage annuloplasty techniques also include other cerclage trajectories.

Components of the device disclosed herein can be made of an "MRI-compatible" material. Such materials are safe to use in the body during magnetic resonance imaging of the body, and do not substantially affect imaging quality of the MRI. An "MRI-safe" material is one that does not add substantial risk to a human or equipment by placing it in the magnetic field of an MR environment. Examples of MRI-compatible materials are non-ferrous materials, such as ceramics, plastics and non-magnetic composite materials. Austenitic stainless steels (of the 300 series) are neither ferromagnetic nor paramagnetic and therefore are MRI-compatible. Titanium and aluminum are MRI-compatible, even though they are not ideally paramagnetic. Particularly disclosed MRI-compatible materials of which the protective device may be made include nitinol, MP35N and cobalt-chromium alloys.

The term "protection member" refers to an element that is designed to cooperate with the tensioning element to provide a protected space to a blood vessel or other vital structure along the path of the tensioning element. In general, the protection member is designed so that the blood vessel or vital structure within the protection member experiences less force from the tensioning element than is exerted at adjacent areas at either end of the protection member.

A "shape memory" material has the ability to return from a deformed shape (temporary shape) to its original (permanent) shape in response to a trigger, such as a physical or thermal trigger, for example release of the material from physical constraint within a catheter lumen. Shape memory materials are typically made of alloys or polymers. In specific examples, the material is a superelastic nickel-titanium alloy such as nitinol or a nickel-chromium alloy such as inconel.

As used herein, the term "suture" or "ligature" is meant to encompass any suitable cord-like material and is not limited to only twisted strands, fibers of plastics. A suture is not used in the limited sense of a material that is moved through tissue on a surgical needle to penetrate tissue, but instead more broadly encompasses sutures that are used to encircle and/or compress an organ (as in cerclage of the uterus, ligation of a duct, or mitral or tricuspid annuloplasty of the heart). Both of the terms "suture" and "ligature" include metal and non-metal materials, wire or non-wire materials, natural and synthetic materials, absorbable and non-absorbable that are suitable for ligation or placement of tension or compression on a target structure within the body of a subject. In some embodiments, the suture is a thin and elongated cord. An example of a wire suture or ligature is an annuloplasty wire while examples of non-wire sutures are those made of catgut, silk, polyester, polyglycolic acid, polylactic acid, polydioxanone, nylon, and polypropylene. A variety of suture materials are supplied under names such as ETHILON, MONOCRYL, PROLENE, or VICRYL. Wire sutures are typically made of stainless steel, and can be similar to those used for orthopedic surgery or sternal closure.

"Target structure" includes both biological and non-biological materials. A biological target structure is made of biological tissue, for example an anatomic structure in the body of a subject. Such anatomic structures preferably have a base portion connected to the body and a free portion over and around which the loop can be placed. Examples of the target structures are a body organ, a portion of a body organ, or a surgically implanted device. Anatomic target structures include a heart or atrial appendage, a cecal appendix, a gallbladder, a neoplasm, a uterus, a hemorrhoid, an uvula, an aneurysm, a transected blood vessel or other transected, folded or looped lumen, an intraocular crystalline lens, a urinary bladder, a kidney, or a prostate gland. Targeted neoplasms particularly include examples such as a polyploid or sessile neoplasm. Examples of a non-biological target structures are items that have been surgically or accidentally introduced into the body, such as a projectile or a displaced surgical implant.

"Tensioning material" is any material suitable to place compression on an object (such as an organ) around which it is looped. For example, the tensioning material may be suture that is wrapped around the uterus to perform a B-Lynch procedure to mechanically compress an atonic uterus and stop postpartum hemorrhage, or a mitral or tricuspid valve cerclage annuloplasty, in which an encircling material is placed under tension to remodel the mitral valve annulus.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. The term "comprising A or B" refers to a single element of stated alternative elements or a combination of two or more elements, unless context clearly indicates otherwise. For example, the phrase "rtMRI or echocardiography" refers to real-time MRI (rtMRI), echoradiography, or both rtMRI and echocardiography. Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

Exemplary Encircling Implant Delivery Systems and Methods

Figure 2:
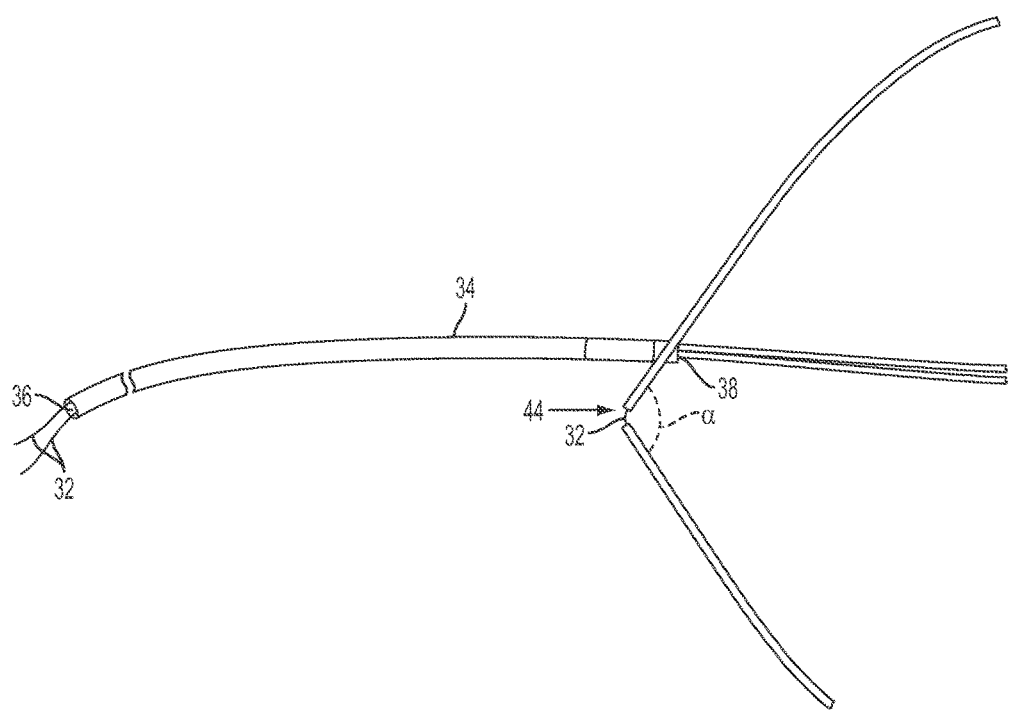
FIG. 2 is an enlarged view of the articulation tip of the device of FIG. 1, with the arrow indicating the suture extending through the interior of the distal limbs and being exposed only at the articulation tip. The free terminal ends of the suture are shown emerging from the open proximal tip of the catheter; the catheter is shown schematically shorter than in actual use.
Figure 3:
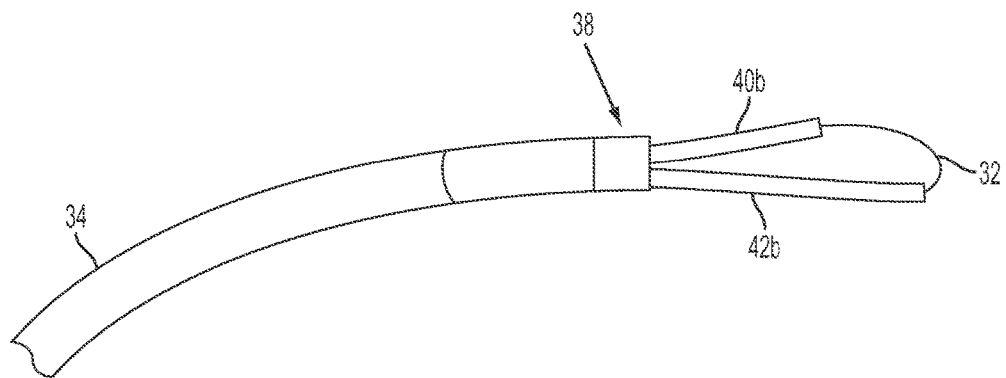
FIG. 3 is a view of the limbs retracted into the delivery catheter with only the articulation tip extending from the open distal tip of the delivery catheter, and illustrating how the assembly collapses for transcatheter delivery.

One exemplary embodiment of an encircling implant delivery device is shown in FIGS. 1-3, which depict a device 30 for delivering an encircling continuous flexible suture, wire, strip, cord, tube, line, or other encircling implant (referred to herein generally as suture 32) around a portion of a target structure (not shown) in a subject's body. The illustrated device 30 includes an elongated, flexible tubular delivery catheter 34 (FIG. 2) having a continuous lumen that begins at a proximal open tip 36 for controlling the catheter and terminates at an open distal delivery tip 38 that is suitable for introduction into the body. The catheter is made of a biocompatible material, and may for example be a flexible cardiovascular catheter that can be introduced over a guide wire and/or through a guide sheath. Within catheter 34 are separate first and second delivery limbs or arms 40, 42 maintained in an articulating relationship at an articulation tip 44 (FIGS. 1 and 2) by suture 32 that extends through first and second delivery limbs 40, 42. The terms "limb" and "arm" are used interchangeably herein. Since delivery limbs 40, 42 are not otherwise joined to one another by a coupling at the tip 44, limbs 40, 42 can slide freely along suture 32 toward or away from one another. Hence limbs 40, 42 are capable of being folded together substantially parallel to one another while sliding through catheter 34, but are capable of articulating with respect to one another once they emerge from distal tip 38 of catheter 34. In other embodiments, the delivery limbs 40, 42 can have distal ends that join with a common trunk and/or proximal portion that extends through the catheter, these portions together comprising a guide for delivering the implant.

Although suture 32 can be made of any of the variety of materials previously discussed, the illustrated suture 32 is made of wire material, such as wire suture of the type used as a ligature in coronary sinus annuloplasty procedures. The suture 32 has first and second free terminal ends (FIG. 2) extending from proximal tip 36 of delivery catheter 34. Between the first and second free terminal ends, the suture 32 extends continuously in a loop through limbs 40, 42 and within delivery catheter 34.

Each limb 40, 42 includes a proximal limb portion 40a, 42a (FIG. 1) and a distal limb portion 40b, 42b. The proximal and distal limb portions can be made of the same or a different material, and in the illustrated embodiment are made of the same material, which in this example is a nitinol hypotube. However, other elastic or superelastic materials can be used. Proximal limb portions 40a, 42a have a longitudinal shape that can conform to the shape of the lumen of the delivery catheter. They are contained in substantially parallel relationship within the lumen as they move through the lumen and can continue to maintain that relationship even after the proximal limb portions 40a, 42a partially emerge from catheter 34, as shown in FIG. 1. Proximal limb portions 40a, 42a can be connected together in at least one location (for example by a collar, as discussed later in association with FIGS. 9-12) to constrain rotation of the first and second delivery limbs with respect to one another.

Flexible distal limb portions 40b, 42b are resiliently deformable into a substantially parallel delivery shape to extend along the longitudinal axis of the flexible delivery catheter (FIG. 3), but assume the shape of a loop (FIG. 1) cooperatively formed by the flexible distal limb portions 40b, 42b when they are not deformed into the delivery shape. For example, limbs 40, 42 (or at least distal limb portions 40b, 42b) can be made of a shape-memory material that is deformable into the parallel delivery shape that conforms to the path of the catheter, but when not constrained by the walls of the lumen distal limb portions 40b, 42b cooperatively form the loop. The loop shape can be preselected and preconfigured to assume a shape and size substantially complementary to a feature of the target structure. In the illustrated embodiment of FIGS. 1-2, the loop assumes the shape of a cross-section of the heart around the atrioventricular groove of the heart.

Figure 4:
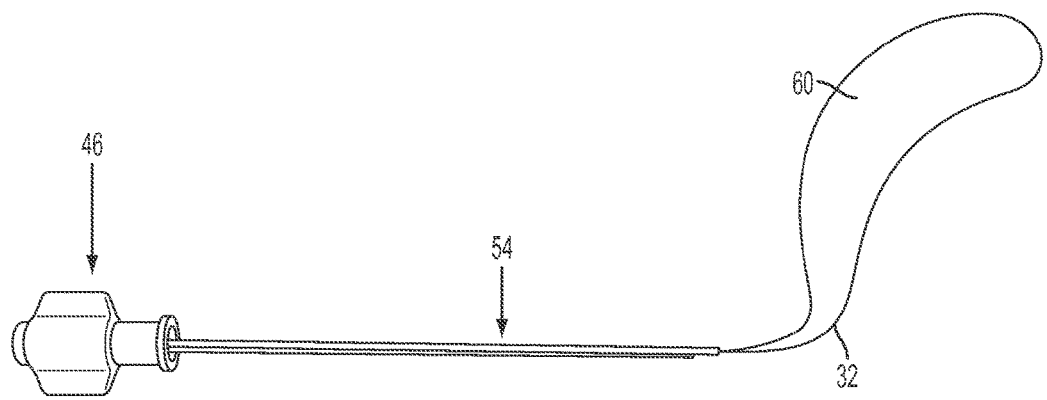
FIG. 4 is a view of an assembled embodiment of the delivery device in which the delivery catheter is a 7 French (F) introducer sheath having a hollow shaft through which the delivery limbs are advanced to deliver the suture loop, which is shown at the right margin of the figures.

FIG. 4 illustrates another exemplary delivery device comprising a rigid metal tube or needle 54 extending distally from a proximal hub 46. The limbs of this delivery device have been independently retracted into and through the tube or needle 54, so that the remaining suture 32 forms loop 60. This delivery device can be used for surgical or percutaneous delivery methods, for example.

Figure 6:
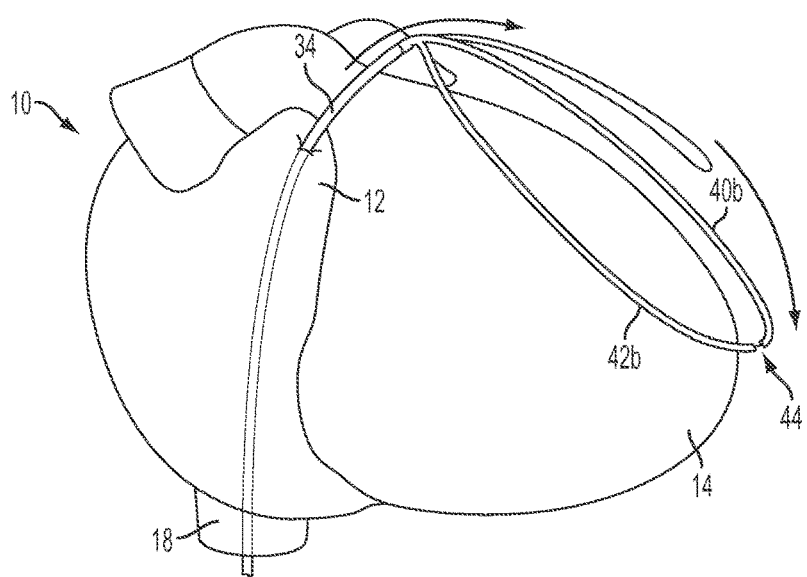
FIGS. 6 and 7 show a view of the heart and illustrate deployment of the limbs by further advancement of the articulation tip out of the catheter to allow both distal limbs to assume their preconfigured and unconstrained loop configuration, and advancement of the loop along the external wall of the heart and over the apex to encircle the heart. The preformed shape of the limbs allows it to surround the target structure (in this case the heart) and further be manipulated to its targeted position (in this case the atrioventricular groove).
Figure 7:
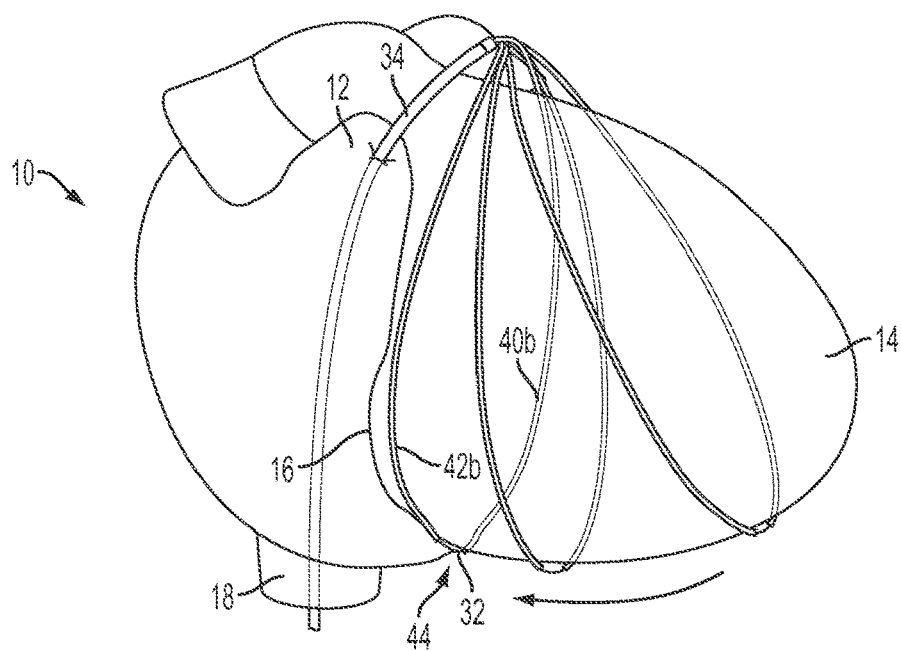
Figure 8:
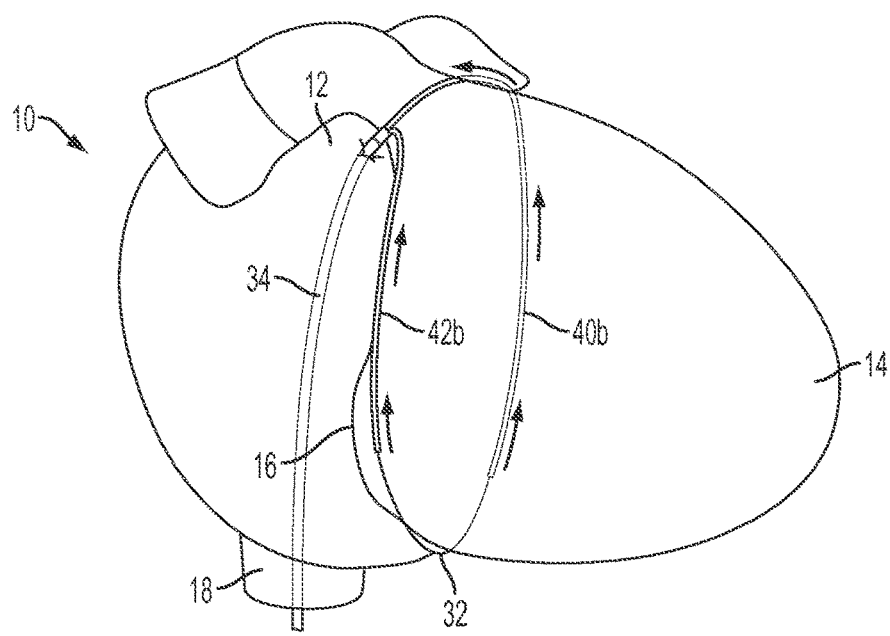
FIG. 8 shows the partial retraction of the limbs over the suture to leave the exposed suture in the desired position around the heart along the path defined by the placement of the limbs around the heart. The suture is maintained at a desired (for example constant) tension as the limbs are retracted from the suture to maintain the suture in the desired position. This allows the suture to be positioned precisely in the target position. After the limbs are fully withdrawn, the desired tension can be fixed on this suture using a tension fixation mechanism such as a separate device or knot.

Returning to the embodiment of FIGS. 1-3, an exemplary method of delivery for a suture encirclement procedure can include the following steps, with reference to FIGS. 6-8. A guide wire can be introduced into a vein (such as the femoral vein) and advanced through the interior vena cava 18 to the right atrial appendage 12 of the heart 10, such as under fluoroscopic guidance. The wire can then pierce through the right atrial appendage 12 and into the pericardial space if the pericardium is present. An introducer sheath is advanced over the guide wire into the pericardial space, and contrast material can be injected into the pericardial space through a lumen of the catheter to visualize the cardiac contours. Catheter 34 is then advanced through the introducer sheath until distal tip 38 is also extending out of the right atrial appendage 12 and into the pericardial space.

Figure 5:
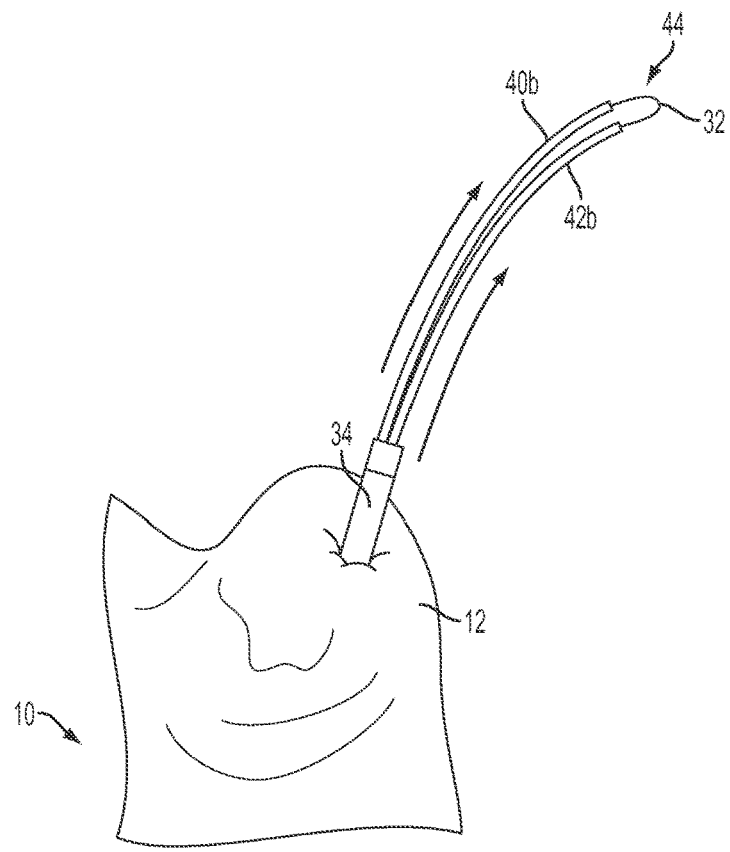
FIG. 5 is an enlarged view of the atrial appendage illustrating the initial deployment of the limbs through the catheter that extends through the right atrial appendage into the pericardial space. An introducer sheath passes from the right atrial appendage into the pericardial space. Through this introducer sheath the device is advanced in a folded or constrained state into the pericardial space for deployment. Both limbs and the suture-articulation are shown in the drawing.

FIG. 5 is an enlarged view of the atrial appendage 12. The catheter 34 has been advanced through the wall of the atrial appendage 12 to introduce the distal tip of the catheter into the pericardial space. The distal limbs 40b, 42b can then be deployed by withdrawing catheter 34 from the pericardial space to unsheathe distal limbs 40b, 42b. Alternatively, once the catheter is in place, the articulation tip 44 of the distal limbs 40b, 42b can be advanced out of the open catheter tip in the direction shown by the arrows in FIG. 5. As the distal limbs advance out of the catheter, they begin to move apart from their parallel delivery configuration toward their unconstrained configuration predetermined by the shape memory material of which they are made.

FIGS. 6 and 7 show the heart 10 with the apex 14 of the heart pointed toward the right. As the distal limbs 40b, 42b are further deployed from the catheter 34, they move farther apart to their unconstrained configuration predetermined by the shape memory material. As shown in FIG. 6, the two distal limbs articulate farther part at the articulation tip 44 where the ends of the distal limbs are held together by the continuous suture 32 that extends through the limbs. As the limbs articulate apart at the articulation tip, they also spread the suture contained within the limbs. Advancement of the distal limbs moves the articulation tip toward the apex 14 of the heart (FIG. 7) and over it.

As articulation tip 44 of the limbs is unsheathed by catheter 34, the shape memory material begins to spread distal limbs 40b, 42b apart (FIG. 6) to a maximum angle a (FIGS. 1 and 2), such as approximately 50-55 degrees in one embodiment. In this particular embodiment, each distal limb 40b, 42b assumes an arcuate or semi-lunar shape, with each limb a mirror image of the other, as shown in FIG. 1. Each of the illustrated semi-lunar shapes can be planar, and the planes defined by each of distal limbs 40b, 42b may either be co-planar or at a non-coplanar angle to one another. The arcuate segment formed by each distal limb 40b, 42b begins at a junction between the proximal and distal limb portions and the arcuate segments end at or adjacent the articulation tip of the delivery limbs. The distal limb portions 40b, 42b are retained in the articulating relationship solely by the suture 32 to be delivered that extends through the limbs and spans a gap 44 between the distal limb portions.

As shown in FIGS. 7 and 8, the shape memory material is configured in its unconstrained configuration so that the plane of the loop defined by the distal limbs bends toward the catheter 34 and the proximal limbs to promote movement of the loop over the apex 14 of the heart and along the external wall of the heart contralateral to the wall along which the loop was advanced in FIG. 6.

Distal limbs 40b, 42b can comprise a resilient elastic or superelastic material that is configured to deflect back toward the delivery catheter 34 as the distal limbs emerge from the distal delivery end of the delivery catheter 34, as shown in FIGS. 6 and 7. During this deflection, distal limbs 40b, 42b move (within the pericardium if it is present) down toward the apex 14 of the heart and past it to then encircle a circumference of the heart 10 (FIG. 7). Distal limbs 40b, 42b can be positioned around the heart substantially in its atrioventricular groove 16 is some procedures, such as for an annuloplasty procedure.

Once the limbs 40b, 42b are in a desired target position, such that the limbs and the suture 32 that are contained therein encircle the heart, which can be confirmed by fluoroscopy, the limbs 40, 42 are withdrawn over the suture 32 through catheter 34 by sliding limb 40 towards one proximal terminal end of the suture and sliding limb 42 towards the other proximal terminal end of the suture (FIG. 8). The separate limbs are removed from opposite terminal ends of the suture to leave only cerclage suture 32 encircling the heart 10. The arrows in the FIG. 8 illustrate partial retraction of each limb over the suture back into the catheter 34. The limbs are retracted by manipulating their proximal ends which may be external to the introduction site of the catheter into the body. The limbs can be retracted separately or in tandem, but in the illustrated embodiment of FIG. 8 the two proximal limbs are tethered together so that they are retracted in unison by the operator pulling on them so they slide over the suture. As the distal limbs retract into the catheter, their distal ends move apart from the articulation tip 44 to incrementally expose the suture 32 that they are delivering. As the limbs continue to be retracted, they completely expose the suture 32 such that the suture is left in the same position that the distal limbs occupied before their retraction. After the limbs have been retracted from the suture, the proximal free ends of the suture are then tied or otherwise joined together to retain the suture loop in the final delivery position. The orientation of the loop with respect to catheter 34 can be controlled by moving one or both of limbs 42, 44. For embodiments in which limbs 42, 44 are secured together by a collar or other connector, limbs 42, 44 can be rotated within catheter 34 to change the plane(s) of deployment of the loop. If limbs 42, 44 are not connected together, they can be rotated independently of one another to selectively alter the angle between the plane of each half of the loop.

Once the limbs have been retracted to leave the suture 32 positioned around the target structure, tension can then applied to suture by pulling the free terminal ends of the suture, such as to compress the heart along the atrioventricular groove 16. In some embodiments, a slip knot can be used to tighten the suture loop by pulling on only one end of the suture. The suture 32 can be tied either by a locking mechanism (similar to a drawstring toggle) or a simple surgical knot. The free ends of the suture 32 proximal to the locking mechanism or knot can then be cut with a cutting device.

Although the disclosed encircling suture devices have been described in connection with the encirclement of the heart, the devices can be used to encircle a variety of target structures. The distal limb portions that form the loop can be pre-configured to assume a shape and size substantially complementary to a circumference or other feature of the target structure around which the loop is to be circumferentially or otherwise navigated or placed. Examples of the target structure are a body organ, neoplasm, or surgically implanted device. Even more particular examples are a heart or atrial appendage, cecal appendix, gallbladder, neoplasm such as a polyp, uterus, hemorrhoid, uvula, aneurysm, transected, folded or looped blood vessel or other lumen, intraocular crystalline lens or implanted intraocular lens or lens haptic, urinary bladder, kidney, prostate or foreign body.

Figure 9:
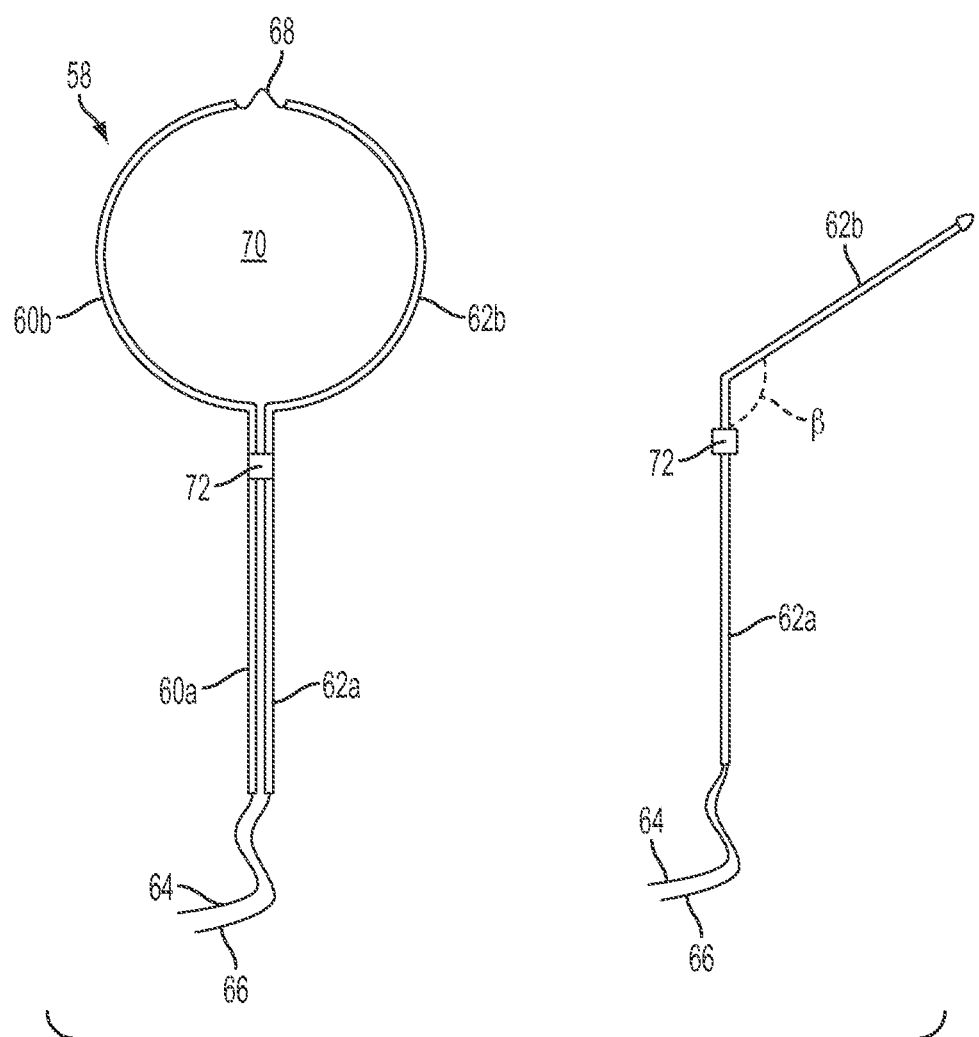
FIG. 9 schematically illustrates a top and side view of an embodiment of the delivery system in which the distal limbs are cooperatively configured to form a circular loop when the distal limbs are not compressed into a substantially parallel and linear delivery shape; the proximal limbs are shown secured together at a fixation point and with the proximal limbs substantially linear and parallel. The suture to be delivered extends through the delivery limbs, joins them at the articulation, and has free ends that extend from the open proximal tip of the limbs.

Another exemplary encirclement suture delivery device 58 is shown in FIG. 9, wherein delivery device 58 includes tubular proximal limbs 60a, 62a and tubular distal limbs 60b, 62b. Terminal ends 64, 66 of a continuous suture extend from the proximal open tips of limbs 60a, 62a. The suture extends across a gap between the open distal tips of limbs 60b, 62b to provide an articulation 68 around which limbs 60b, 62b articulate or pivot with respect to each other. This articulation can be in any direction and is not constrained by a hinge or other similar joint that physically connects limbs 60b, 62b. In this specific example, limbs 60b, 62b each form a minor image, symmetric half of loop 70 for delivering the suture that extends continuously through the tubular delivery device. The halves of the loop are generally symmetric with respect to articulation 68 and a fixation 72 that fixes limbs 60a, 62a together. As shown in the FIG. 9 side view, circular loop 70 is formed in a flat plane that extends at an angle β of about 120 degrees to the plane through limbs 60a, 62a. This arrangement permits the suture within the delivery device to be looped around the target structure in an orientation that is not an extension of the longitudinal axes of limbs 60a, 62a. Limbs 60a, 60b are joined at a fixation that joins the limbs together. The fixation 72 can be, for example, a weld, collar or adhesive that joins limbs together so they move together as they are being pulled off the suture that they are delivering. When the limbs are removed by pulling them off terminal ends 64, 66 of the suture, the suture remains around the target structure at the desired angular orientation.

Figure 10:
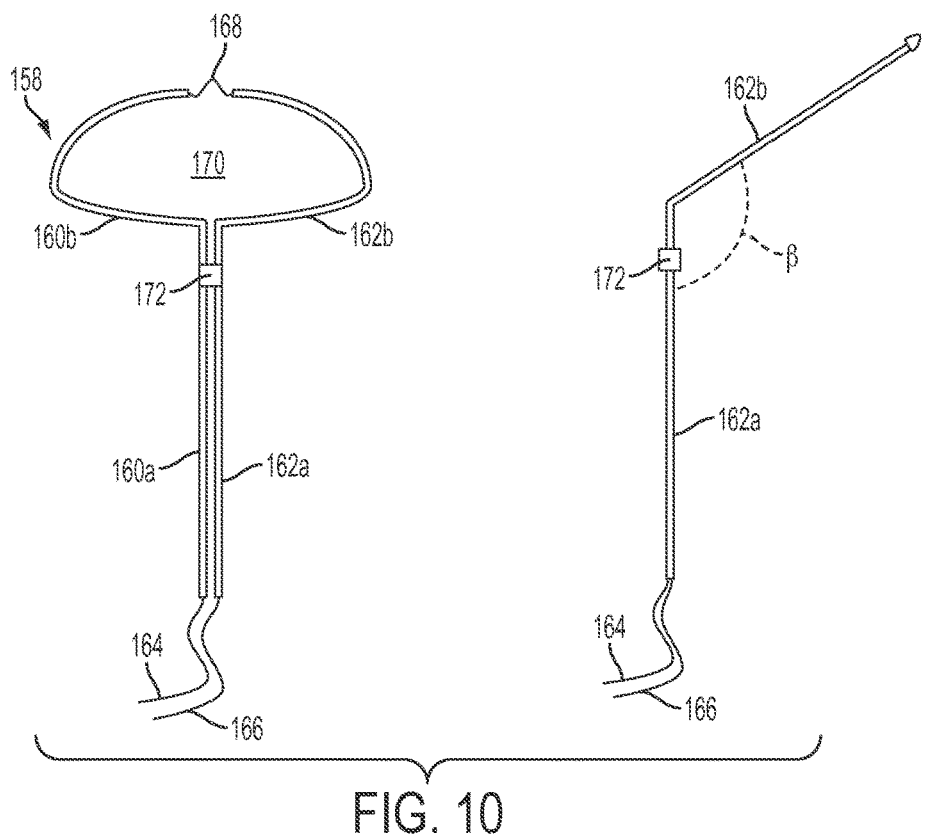
FIG. 10 is a view similar to FIG. 9, but with distal limbs that are cooperatively configured to form a non-circular loop in which the two halves of the loop formed by the distal limbs are mirror images of one another. The loop has both arcuate and relatively flattened portions.

FIG. 10 depicts yet another embodiment of the invention that is similar to that shown in FIG. 9, and in which corresponding parts have been given the same reference numbers as in FIG. 9 plus 100. This embodiment differs in that loop 170 is generally ovoid in shape instead of circular.

Although limbs 160b, 162b still form minor image, symmetric halves of loop 170, which extends at an angle β to the longitudinal axes of limbs 160a, 162a, loop 170 is not circular. It is instead ovoid or oblong, with each half of loop 170 being somewhat U-shaped or V-shaped. Although the halves of loop 170 are symmetric with respect to each-other, they are not themselves symmetric. In the depicted example, each half of the loop has a generally flat portion and an arcuate portion. The flat and arcuate portions meet at a vertex. In other embodiments, each half of the loop can be the shape of a form having a closed base and open arms, such as a C, J, L, or S-shape.

Figure 11:
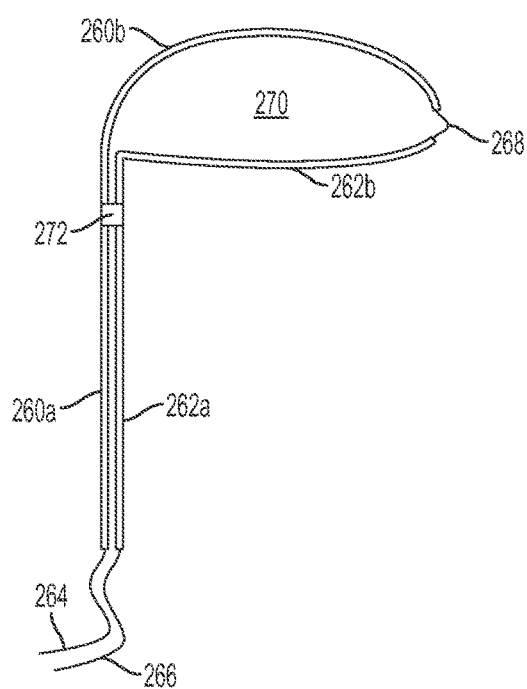
FIG. 11 is a view similar to FIG. 10, but with distal limbs that are cooperatively configured to form an oblong loop in which the two limbs of the loop are asymmetric with respect to one another and generally extend perpendicular to the longitudinal axis of the proximal limbs.

FIG. 11 shows yet another embodiment with an elongated or oblong loop, similar to FIG. 10, and wherein like parts have been given like reference numbers plus 100. However, in this example limbs 260b, 262b do not forms halves of loop 270 that are symmetric minor images of one another. Instead limb 260b forms a hemi-ovoid shape and limb 262b is generally straight or only slightly curved. This pre-configured shape, formed by the shape-memory materials of limbs 260b, 262b when not collapsed to the delivery shape in the lumen of the delivery device, provides a loop 270 that folds to one side of (to the right) of limbs 260a, 262a.

Figure 12:
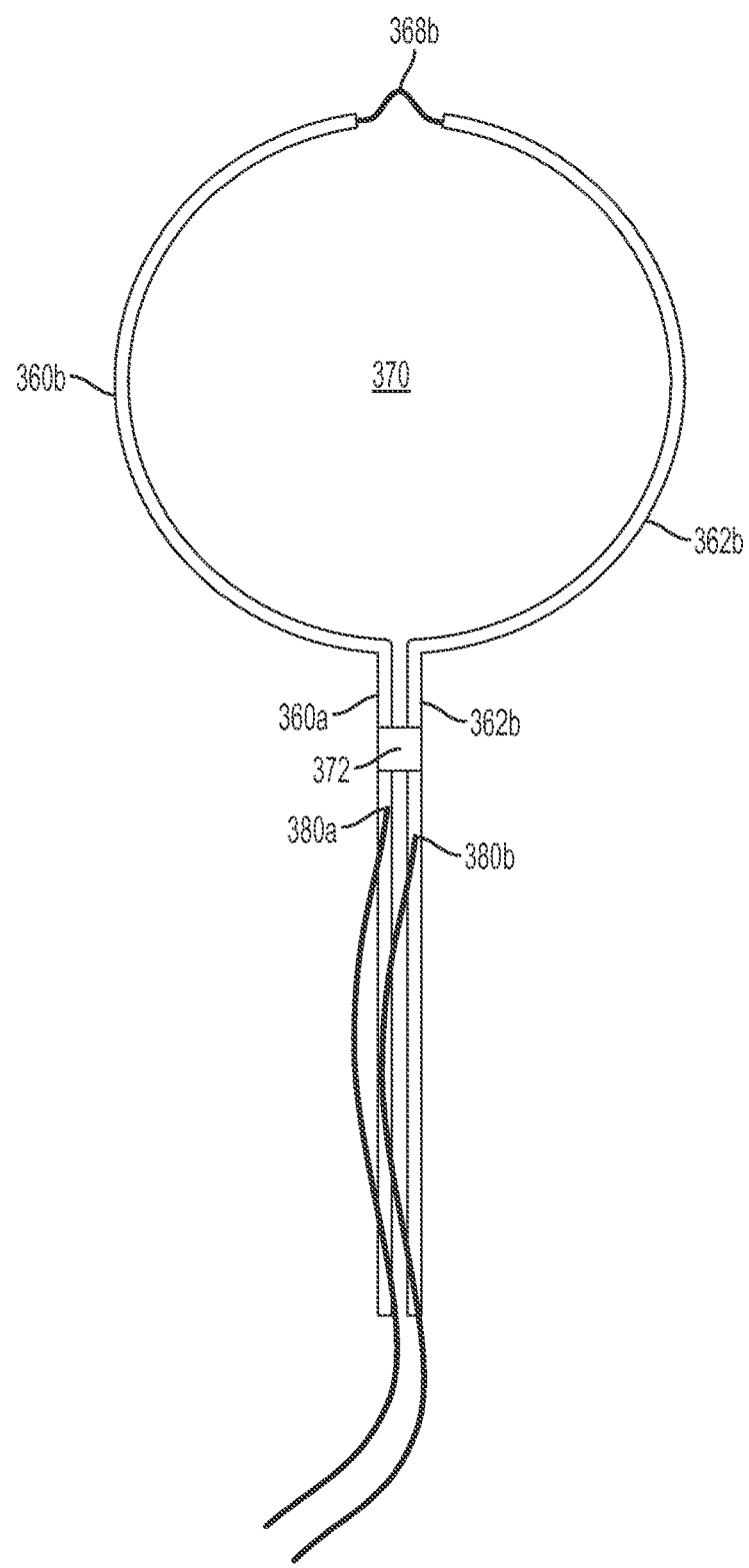
FIG. 12 is an embodiment which is similar to the device of FIG. 9, but the sutures emerge from a limb opening in an intermediate portion of each limb instead of from the proximal tip of the limbs.

FIG. 12 depicts a monorail embodiment of the delivery device similar to FIG. 11, wherein like parts have been given like reference numbers plus 100. In this example, the suture to be delivered extends through limbs 360b, 362b and through only a portion of limbs 360a, 362a. The suture emerges through ports 380a, 380b that are respectively located in an intermediate portion of limbs 360a, 362a that allow the suture to emerge more distally on the delivery device than in the embodiments of FIGS. 9-11 in which the suture emerges from the open proximal tip of each limb. As a result, the limbs ride like a monorail over the suture, and the total length of the suture can be reduced.

Figure 13:
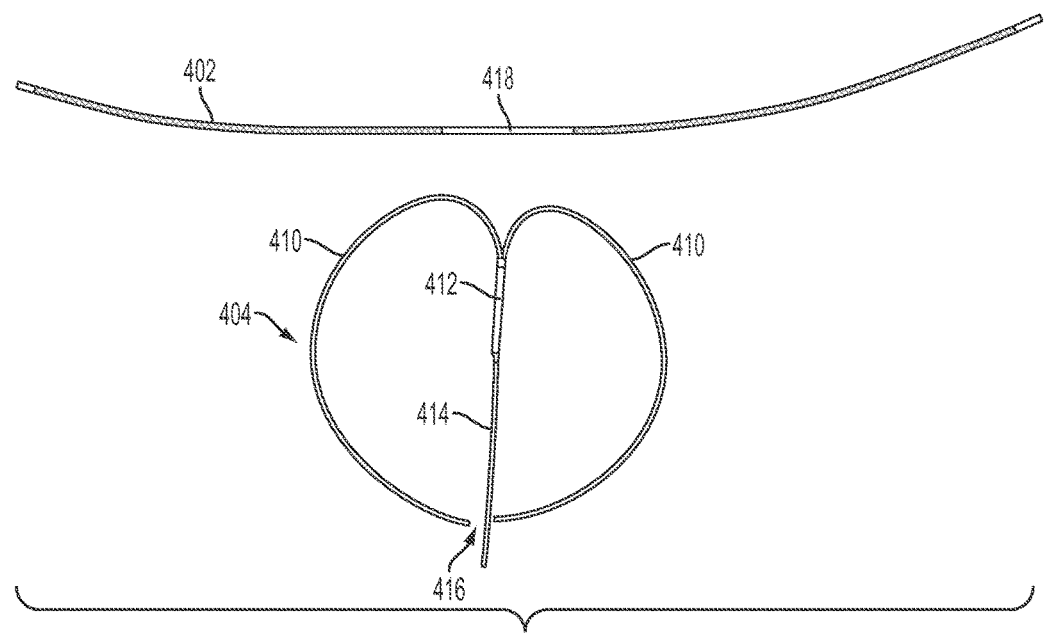
FIGS. 13 and 14 shows an alternative delivery system that includes an interrupted rigid loop having two arms, a suture, and a braided tubular implant positioned around the rigid loop and the suture.
Figure 14:
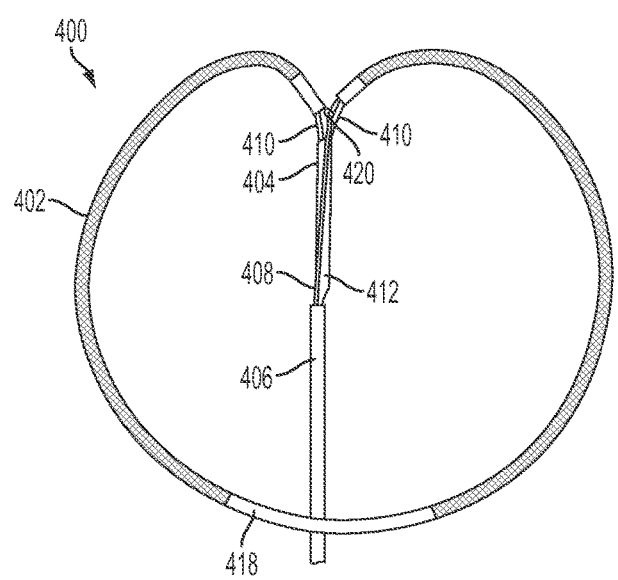

FIG. 14 shows another exemplary encircling implant delivery device 400, and FIG. 13 shows elements of the device 400 disassembled. The device 400 is configured to deliver a tubular implant 402 around the anatomical target. The device 400 also includes a resiliently deformable guide 404 (FIG. 13), a catheter 406, and a suture or other cord 408. The guide 404 includes two distal arms 410 extending from a common trunk 412 and a proximal portion 414 extending through the catheter 406. The arms 410 form a natural loop configuration (FIG. 13) when not deformed such that free ends of the two arms are adjacent each other but not attached, forming a break or gap 416 in the loop between the free ends of the arms. The tubular implant 402 is positioned over the arms 410 such that a central portion 418 of the tubular implant bridges the gap 416 and the two ends of the tubular implant are adjacent to the trunk 412 (FIG. 14). The suture 408 includes a loop that extends through the tubular implant 402 and a proximal strand that extends from the loop at joint 420, and extends through the catheter 406.

For delivery into a patient's vasculature, the implant 402, guide 404, and suture 408 are deformed and contained within the catheter 406 in a straightened configuration. While contained within the catheter 406, the arms 410 are resiliently deformed to extend distally in parallel in front of the trunk 410, with the gap 416 allowing the distal ends of the arms to be pointed distally side-by-side. The tubular implant is folded at the central portion 418 such that the central portion spans across the two distal ends of the arms 410 and the two ends of the tubular implant 402 extend proximally from the central portion 418 over the arms 410 in parallel within the catheter 406. The suture 408 extends through the folded tubular implant 402 in the same elongated configuration.

The tubular implant 402 can comprise any sufficiently strong, flexible, and biocompatible material to allow it to be implanted around a target structure and desirably tensioned. In some embodiments, the tubular implant 402 comprises a braided or woven material, while in other embodiments the tubular implant can comprise non-braided, non-woven continuous tube. In some braided or woven embodiments, tubular member 402 can be configured to be compressible and/or elongatable in the longitudinal direction of the implant, such as in order to accommodate reduction in the circumference around the target structure as the implant is tightened around the target structure. In some embodiments, the length of the tubular implant can be shortened by 50% or more relative to its length in a natural configuration. Such variability in length can allow the tubular implant 402 to avoid buckling or kinking when it is tightened around the target structure. In some embodiments, as the length of the tubular implant 402 is shortened, the diameter of the tubular implant can increase in a corresponding manner, while in other embodiments, the diameter of the implant can remain substantially constant as the length changes. In some embodiments, the diameter of the tubular implant in its natural configuration can be about 2-5 mm, such as about 2-3 mm. In some embodiments, the tubular implant 402 can comprise a superelastic and/or shape memory material, such as braided nitinol, which can provide the implant with resilient deformability and help it to return to a natural shape (e.g., the shape shown in FIG. 14) when it is released from the delivery catheter 406, and can allow the implant to re-lengthen from a compressed state if tension around the target structure is released. The central portion 418 of the tubular implant can comprise a readily bendable and foldable tubular section that allows the central portion 418 to be folded 180 degrees while it is positioned within the delivery catheter.

The guide 404 can comprise any semi-rigid, resiliently deformable material, such as an elastic or superelastic metal, such nitinol. The arms 410 and other portions of the guide 404 can comprise solid rods, as they need not allow passage of another object within them. The suture 408 and the arms 410 can extend in parallel through the tubular implant 402. In other embodiments, the arms 410, trunk 412, and/or proximal portion 414 of the guide 404 can be tubular. In such embodiments, the suture 408 can extend through the tubular portions of the guide 404.

In the illustrated embodiment, the suture 408 extends alongside the arms 410 within the tubular implant 402 and joins at a knot or a sliding-locking device 420 near the juncture of the arms 410 and the trunk 412, with a proximal strand of the suture extending alongside the trunk and proximal portion 414 of the guide. The joint 420 can comprise a sliding Roeder's knot, or a slip knot, a device that allows for tightening and/or locking, or other adjustable feature that allows the circumference of the loop portion of the suture within the tubular implant 402 to be adjusted. For example, one end of the suture can include a knot or device at 420 and the suture can extend from the knot or device 420 around the circumference of the implant 402, through the knot or device 420, and extend proximally to a second end of the suture, similar to as shown in FIG. 14. In such embodiments, the single proximal end 408 of the suture can be pulled through the knot or device 420 to reduce the circumference of the loop portion of the suture, thereby tightening the implant around a target structure. In alternative embodiments, the suture can extend from one proximal end, with an intermediate loop portion extending through the tubular implant 402, and back to a second proximal end running parallel with the first proximal end. In such embodiments, both ends of the suture can pass through a knot or device at 420 that allows for tightening of the intermediate loop portion by pulling on either or both of the proximal ends of the suture.

FIGS. 15-21 show an exemplary delivery method with the device 400, wherein the tubular implant 402 is implanted around the heart 10 at or near the atrioventricular groove 16 of the heart. FIG. 15 shows the catheter 406 extending through an aperture in the right atrial appendage 12 and into the intrapericardial space. The delivery device 400 can be introduced through any portion of the venous system, such as through the inferior vena cava 18, and then through the right atrial appendage 12. As shown in FIG. 15, the tubular implant 402 is advanced distally out of the catheter 406 in a folded configuration with the central portion 418 leading. The arms 410 of the guide 404 are positioned within each parallel half of the implant 402, though not visible in FIG. 15.

FIG. 16 shows the implant 402 being further deployed from the catheter 406 such that the implant and arms 410 within the implant begin to resiliently return to the configuration shown in FIG. 14. As shown, the distal end of the implant 420 recoils down and around the apex 14 of the heart as the implant expands apart to form a loop shape. The resilient nature of the arms 410 and/or the resilient nature of the tubular implant 402 (e.g., either or both can comprise nitinol or the like) can facilitate the motion of the implant shown in FIGS. 16 and 18.

FIG. 17 is a partially broken-away view of the central portion 418 of the tubular implant 402, showing the distal ends of the two arms 410 positioned within the implant and spaced by 416, and showing the suture 408 running through the implant alongside the arms 410.

Figure 18:
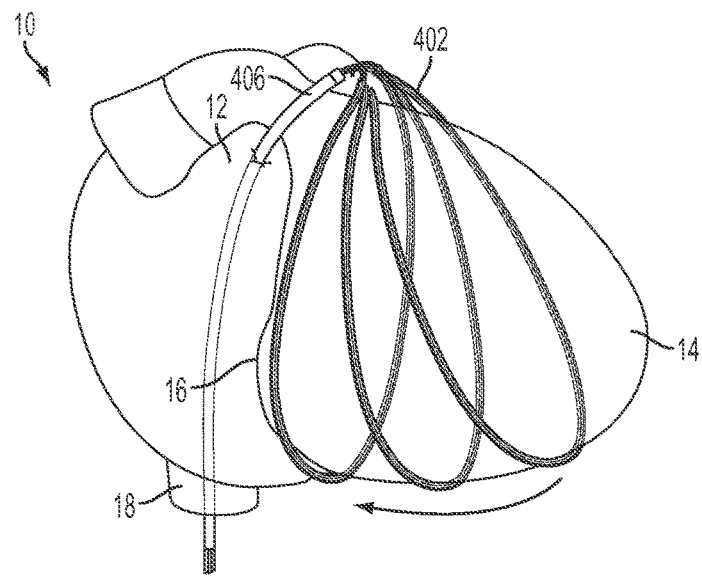

FIG. 18 shows the implant 402 resiliently articulating further toward the configuration shown in FIG. 14, with the central portion 418 of the implant moving toward the catheter 406. This resilient motion directs the implant 402 toward and around the atrioventricular groove 16 of the heart.

Figure 19:
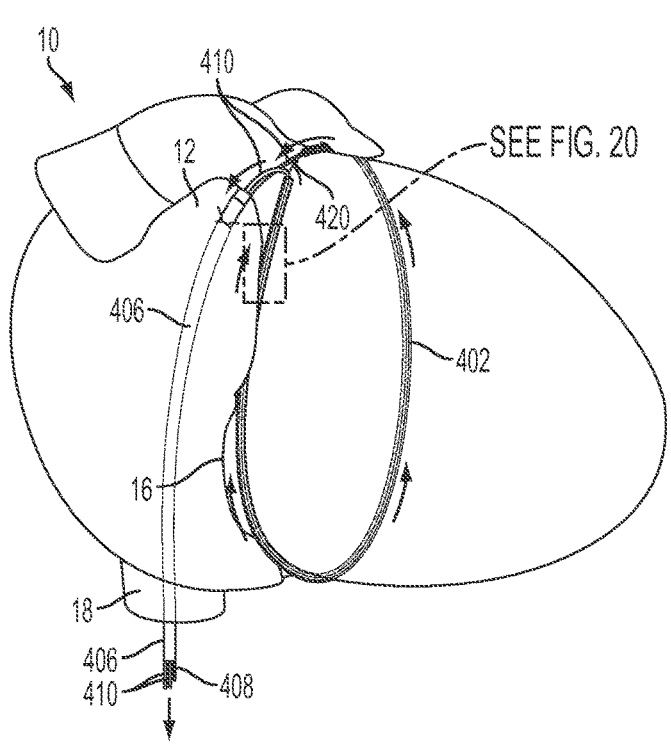
FIGS. 19 and 20 show retraction of the rigid arms from within the tubular implant to leave the implant and suture in the desired position around the heart.
Figure 20:
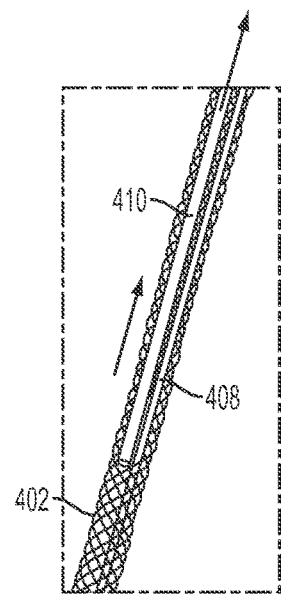

FIG. 19 illustrates the guide arms 410 being retracted out of the tubular implant 402 after the implant has been positioned at the desired implantation site adjacent to the atrioventricular groove 16. The proximal portion 414 and trunk 412 of the guide 404 are retracted proximally through the catheter 406, which pulls the two arms 410 out of the tubular implant 402 around either side of the heart. The break 416 between the arms 410 allows the arms to be retracted out of the implant 402 in opposite directions on either side of the heart. As the arms 410 are retracted, the implant 402 and suture 408 are left encircling the heart. FIG. 20 is a partially broken-away view of a section of the tubular implant 402, illustrating the motion of one of the arms 410 through the implant alongside the suture 408.

Figure 21:
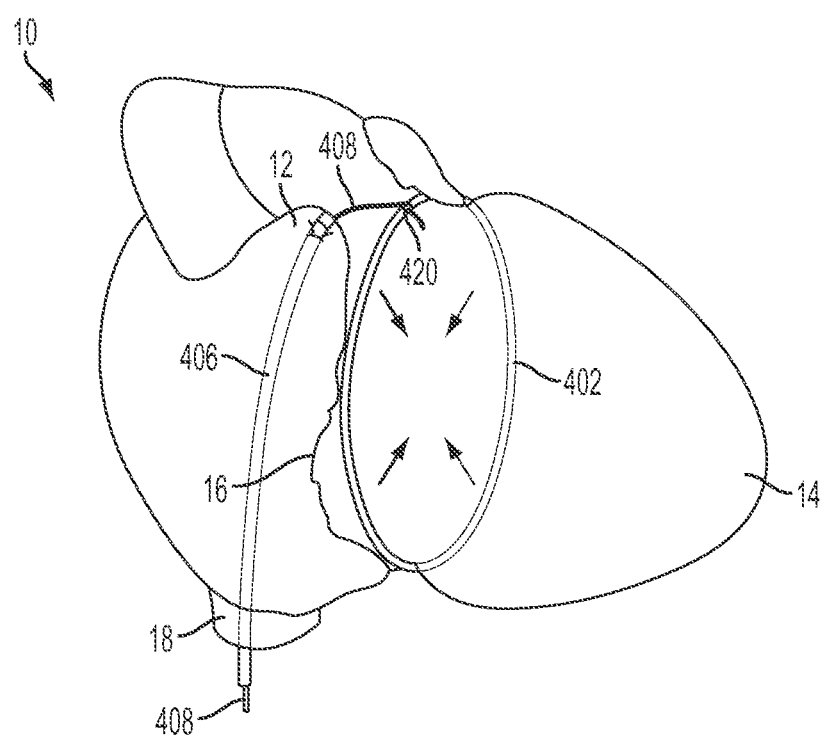
FIG. 21 shows the implant and suture in place around the heart after the rigid arms have been withdrawn. A desired tension can be applied to the implant by the suture using a tension fixation mechanism such as a separate device or a slip knot. The implant can have a braided structure that allows it to shorten when tension is applied without buckling or "cheese wiring" of the heart tissue.

As shown in FIG. 21, after the arms 410 are fully retracted out of the tubular implant 402, the implant is fully deployed from the catheter 406 and the suture 408 remains extending through the implant and through the catheter. The proximal portion of the suture 408 can then be tensioned or pulled to tighten the implant 402 around the heart. The knot or device 420 allows the circumference of the looped portion of the suture to be reduced via tension in the proximal portion of the suture, and reduction in the circumference of the looped portion of the suture causes the implant 402 to also be tightened around the heart to a desired degree, as illustrated by the arrows in FIG. 21. Tightening the implant 402 around the heart brings the two ends of the implant towards each other to more fully encircle the heart. Once the desired degree of tightening of the implant 402 is achieved, the knot or device 420 can be secured or fastened to fix the circumference of the suture and implant around the heart. As described above, the implant 402 can foreshorten as the suture is tightened due to the braided or woven configuration of the implant, preventing the implant from kinking or buckling. The implant 402 also prevents the suture 408 from directly contacting the heart tissue (except for possibly a short segment near the knot or device 420), which prevents the suture from cutting into, or "cheese wiring" into, the myocardium and/or other heart tissue. The implant 402 instead provides a greater surface area in contact with the heart tissue to reduce pressure on the heart tissue and minimize local trauma to the tissue.

Figure 22E:
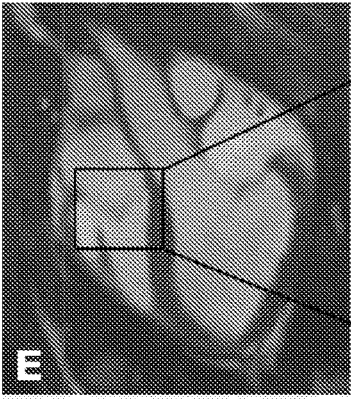
Figure 22F:
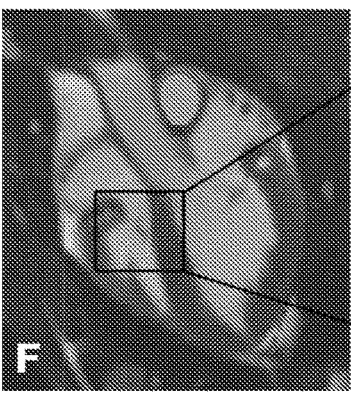

FIGS. 22A-F are MRI images showing views of the heart anatomy before and after an encircling implant 402 is applied around the heart. Significant changes in valve annulus dimensions and valve leaflet coaptation are observed as a result of the encircling implant. FIG. 22A is a 5 chamber view at baseline. The arrow denotes the tricuspid annulus. FIG. 22B is a 5-chamber view after annuloplasty, showing a reduced tricuspid valve annulus diameter. FIG. 22C is a 2-chamber view at baseline. FIG. 22D is a 2-chamber view after annuloplasty, showing a reduced tricuspid valve annulus diameter. FIG. 22E shows tricuspid leaflet coaptation at baseline, with the arrow denoting the length of coaptation. FIG. 22F shows increased tricuspid leaflet coaptation after annuloplasty.

FIG. 23 includes graphs and images illustrating geometric changes to the heart resulting from placement of the encircling implant 402. FIG. 23A shows mean tricuspid valve annular dimensions in 5 and 3-chamber MRI views. The left side of FIG. 23A shows septal-lateral dimensions, and the right side of FIG. 23A shows antero-posterior dimensions. FIG. 23B shows mean mitral valve annular dimensions in 4 and 2-chamber MRI views. The left side of FIG. 23B shows septal-lateral dimensions, and the right side of FIG. 23A shows antero-posterior dimensions. Annular dimension measurements are performed in mid-systole. In both the tricuspid valve and the mitral valve, annular dimensions are significantly decreased from the baseline measurements (left column in graphs) to the post-implantation (middle column) and follow-up measurements (right column). "*" indicates $p<0.05$ and "**" indicates $p<0.001$.

Figure 24:
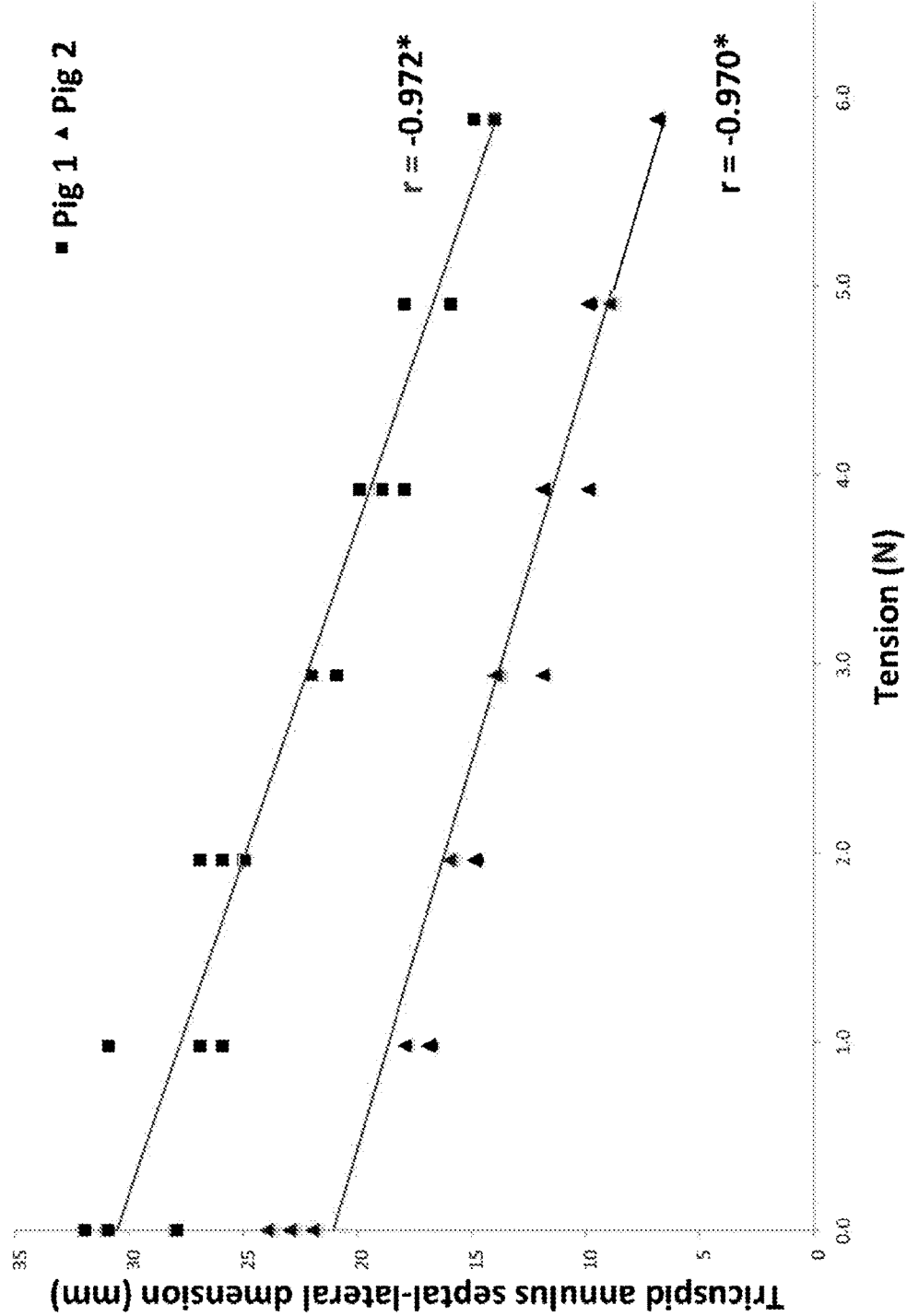
FIG. 24 is a chart showing tension vs. tricuspid annular geometry relationships in test pigs.

FIG. 24 is a chart showing the amount of tension applied to the encircling implant compared to tricuspid annulus septal-lateral dimensions, in two test pigs. Tensioning the encircling implant was measured using a force meter attached to the suture, and was performed three times at each different level of tension, for each test pig. The suture was released back to a relaxed state in between each cycle. "*" indicates $p<0.001$. The chart of FIG. 24 clearly illustrates that the annulus dimensions decreased as tension in the implant increased. As with other embodiments described herein, the device 400 can optionally include compressive elements and/or bridge elements positioned around, within, and/or embedding in the tubular implant 402. Such elements, as described in U.S. Pat. No. 8,211,171, which is incorporated by reference herein, can be positioned various locations around the heart and used to exert compressive remodeling forces at desired locations on the heart and/or used to provide a bridge over sensitive areas, such as a coronary artery, where application of pressure is not desired.

An exemplary bridge element is shown in FIG. 25E. FIGS. 25A-D show coronary arteries and coronary sinus angiography following annuloplasty with an encircling implant, such as the tubular implant 402. FIG. 25A is a left coronary artery angiogram showing the tensioned encircling implant (arrow). FIG. 25B is a right coronary artery angiogram showing the tensioned encircling implant (arrow). FIG. 25C is a coronary sinus angiogram showing the tensioned encircling implant (arrow). FIG. 25D is a left coronary angiogram with the rigid bridge element of FIG. 25E mounted within the encircling implant (arrow) to prevent left anterior descending coronary artery compression.

Figure 26:
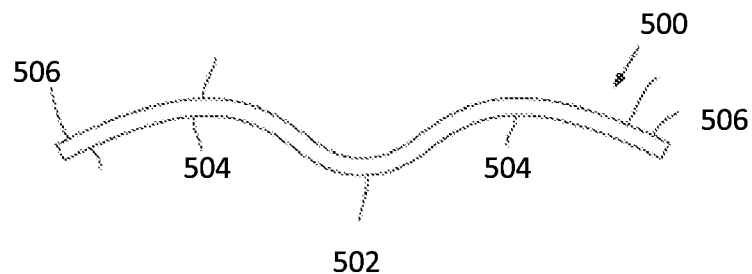
FIGS. 26-28 show examples of compressive members that can be placed along an encircling implant to apply local compressive forces on the target structure.
Figure 27:
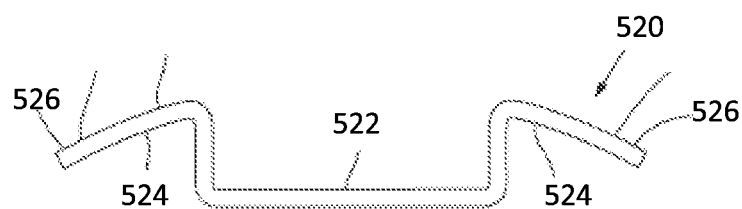
Figure 28:
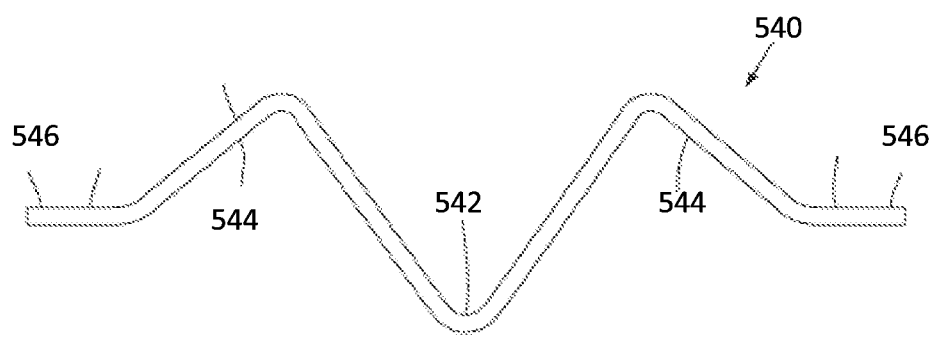

FIGS. 26-28 show exemplary compression members 500, 520, and 540 can be included with the tubular implant 402. The compression member 500 can have an "M" shape with a central projection 502 that presses into the tissue to impart increased pressure, two raised portions 504, and two end portions 506. The raised portions 504 and end portions 506 can generally follow the curvature of the tissue. The compression member 520 can have a similar shape but with a flattened central portion 522 that presses into the tissue to impart increased pressure more evenly over its length. Member 520 also include two raised portions 504 at the ends of the central portion 522, and two end portions 526. The raised portions 524 and end portions 526 can generally follow the curvature of the tissue. The compression member 540 can have a similar shape to member 500 but with a more sharply pointed central portion 542 that presses into the tissue to impart increased pressure, and with more pronounced raised portions 544 and flattened end portions 546.

Exemplary Procedures Using the Disclosed Devices

The disclosed delivery devices and encircling implants can be used in a variety of procedures, such as cardiovascular and non-cardiovascular procedures, where placement of an encircling implant in the body is desired. In addition to other procedures disclosed herein, the disclosed encircling implant delivery devices can be introduced via a delivery catheter through any path through the venous system to the right atrial appendage and through a puncture in the right atrial appendage to access the intrapericardial space, or the devices can be delivered through any portion of the arterial system and into or toward the heart and then delivered through a puncture in the heart wall to access the intrapericardial space, or the devices can be delivered percutaneously directly into the intrapericardial space, or from any other access route into the intrapericardial space. In addition, the disclosed encircling implant delivery devices, or variations thereof, can be used to place encircling implants around any of various other target organs or structures in the body via transvascular or percutaneous delivery routes. In any procedure wherein a puncture or other aperture is formed in the native anatomy, such aperture can be sealed after the implantation of the encircling implant by placement of cardiac closure device, such as nitinol atrial-septal occluder device, or other sealing mechanism.

The methods disclosed herein relative to annuloplasty and other encirclement of portions of the heart can be performed while the heart is still beating, and titrated in real-time to regurgitation under varying loading conditions imposed by hemodynamic provocations such as exercise and volume. This provides a significant advantage over prosthetic valve implantation or other intra-cameral surgical procedures wherein the heart must be at least partially stopped and/or extra-corporeal assistance devices must be used to pump and oxygenate the blood. In addition, methods disclosed herein can avoid long term anticoagulation treatments because the implant is extra-vascular.

The following are several exemplary procedures using the disclosed encirclement implant delivery devices.

A. Transcatheter Mitral Valve Annuloplasty

The delivery devices disclosed herein may be used in methods of improving the function of a mitral valve in a subject in which an annuloplasty implant, for example an encircling implant that exerts compressive remodeling forces on the mitral valve is introduced at least partially around the mitral valve, for example at least partially over the coronary sinus and/or over a coronary artery. The delivery devices can also be used to deploy compressive elements (such as those shown in FIGS. 26-28) around the heart and/or to place protective devices (such as that shown in FIG. 25E) between the encircling implant and the coronary artery, with the encircling implant separated from the underlying coronary artery by the bridge of the device. Compressive remodeling forces can be exerted by the annuloplasty device (for example by applying tension on a tensioning element to alter the shape or configuration of the mitral valve annulus to reduce its circumference) while supporting the annuloplasty element via the bridge to inhibit application of pressure to the coronary artery. The function of the mitral valve in the patient is thereby improved without impairing coronary blood flow.

Briefly described, the encircling implant is introduced at least partially around the mitral valve by advancing the encircling implant in or on the resilient limbs/arms of the delivery device, with the limbs/arms folded against one another in an endovascular delivery catheter. The endovascular catheter is advanced through the vascular system of the subject to the heart, and the distal limbs/arms are deployed from the catheter until they assume the desired shape for guiding the encircling implant around the heart. The encircling implant may include a tensioning element such as a ligature, suture, or tubular body. The tensioning element can extend through or over any protective device that are placed over the coronary artery so that the tensioning element is supported by the protective device. The protective device can optionally also be integrated directly into the tensioning element.

Tension is transmitted through the tensioning element material. Tension can be applied by pulling one or both ends of a suture/cord passing through the encircling implant, or by pulling ends of the encircling implant itself, such as in the case where a tensioning suture passes proximally and is externalized at the point of vascular access. Tension is applied under imaging guidance until the desired degree of mitral annular circumferential reduction is accomplished, or until the mitral valve regurgitation is reduced, or until other endpoints are achieved such as mitral valve inflow obstruction. Tension is secured using a tension fixation device applied to both ends of the tensioning device, such as at the right atrium or right ventricle where the two cerclage trajectories cross, or at the point of vascular access, or in between the two. Tension can be delivered by counter pressure against the fixation device, for example, applied through a delivery catheter. Before fixation, tension can be released or reduced, for example, to reposition the protection device or to achieve a lower degree of mitral annular circumferential reduction.

B. Transcatheter Tricuspid Valve Annuloplasty

The disclosed delivery devices can also be used in Transcatheter Tricuspid Valve Annuloplasty procedures, such as that disclosed in International Patent Application No. PCT/US2014/025300, filed Mar. 13, 2014, which is incorporated by reference herein. In one such procedure, a delivery device delivers an encircling implant including a tensioning element and at least one compression member along the atrioventricular groove of the heart. The tensioning element can comprise a tubular body or a suture/cord delivered through the delivery catheter by deployment of the resilient limbs/arms to position the encircling implant in a desired orientation along or near the heart's atrioventricular groove, and subsequent withdrawal of the limbs/arms to leave the encircling implant around the heart. In embodiments wherein the encircling implant comprises an encircling suture, the compression member can be advanced along the suture and over a desired target position of the atrioventricular groove to apply force to the underlying wall of the heart by selective tensioning of the suture. In embodiments wherein the encircling implant comprises a tubular implant, the compression member can be delivered over or within the tubular implant, or the tubular implant can be pre-configured to include the compression member along its length, such as within, over, or in the wall of the tubular body. The delivery device and encircling implant can alternatively be delivered through a catheter inserted along a trans-thoracic or subxiphoid or subcostal path.

In some embodiments a compression member can be tubular and define a bore dimensioned to allow the encircling implant to pass through the compression member. In some implementations, the compression member has a groove dimensioned to receive the encircling implant and to assist in retaining contact between the tensioning portion of the encircling implant and the compression member. A compression member can incorporate an anti-slip feature configured to contact a surface to reduce slipping of the compression member relative to the heart tissue when the compression member is in position over/under the desired segment with tension applied to the encircling implant. The anti-slip feature can comprise protruding barbs configured to an exterior surface of the heart.

The compression member can have a shaped profile along its length. As illustrated in FIGS. 26-28, the shaped profile can comprise at least two bends, at least one arch, an M-shaped portion and/or at least two inflection points between the segments of different curvatures. The compression member can have a generally curved center segment, a generally straight center segment, and/or a center segment having a vertex. The compression member can have end segments shaped to orient the compression member, and can be self-orienting upon application of tension in a selected location for treatment. The compression element can be resiliently deformable such that the compression member changes from a delivery shape suitable for delivery to a final shape after delivery to a treatment site is complete. The compression member can be at least partially defined by a first major radius of curvature and a second minor radius of curvature.

This procedure can also include the use of a protection member, such as that shown in FIG. 25E, shaped to provide a protected space at least partially accommodating a blood vessel or other vital structure and to receive the tensioning suture or be incorporated into, over, or within, a tubular implant, so that the protection member distributes force developed through increased tension in the tensioning suture to either side of the protected space. As just two examples, the protection member can be configured for positioning over a coronary artery, or over a pulmonary artery trunk.

C. Left Atrial Appendage Ligation

In subjects with atrial fibrillation a thrombus can form in the appendage of the left atrium, and the thrombus can embolize to distant organs. If the embolism travels to the brain, a stroke can occur and result in death or long term disability. Although such patients can be treated with anti-coagulants to help prevent the formation of the thrombus, the use of anti-coagulants can themselves lead to unwanted bleeding, hemorrhagic strokes and death. Surgical methods have been developed to isolate the atrial appendage, for example by suturing or stapling along its base or ostial neck to prevent the flow of blood into the appendage. However, it is desirable to isolate the atrial appendage using minimally invasive or intravascular techniques.

The delivery devices disclosed herein can be used to deliver a tension suture or other encircling implant around the base of the atrial appendage. Once the encircling implant is tightened to compress the base of the appendage, blood cannot flow into the lumen of the appendage and formation of a thrombus is avoided. The encircling implant can be placed around the atrial appendage using a variety of approaches, for example by introducing the delivery catheter through the right atrial appendage. The limbs/arms of the device can then deployed from the tip of the delivery catheter under fluoroscopic guidance, and the distal portions of the limbs/arms (and optionally also the implant itself) can be pre-formed to assume a shape that folds over and loops around the left atrial appendage. The limbs/arms can then be withdraw through the catheter and the encircling implant tightened to close the neck of the appendage and prevent blood pooling in it.

In view of the many possible embodiments to which the principles of the disclosed technology may be applied, it should be recognized that illustrated embodiments are only examples and should not be considered a limitation on the scope of the disclosure. Rather, the scope of the disclosure is defined by the following claims. We therefore claim all that comes within the scope and spirit of these claims.

The invention claimed is:

1. A system for delivering through a catheter an encircling implant around a portion of a target structure in a body, the system comprising:
   a flexible delivery catheter;
   a continuous flexible encircling implant that is to be delivered via the delivery catheter; and
   first and second delivery limbs linked at an articulation region between distal ends of the first and second limbs by the encircling implant and wherein the encircling implant extends over the first and second limbs to maintain the distal ends of the first and second limbs together in an articulating relationship at a distal articulation tip;
   wherein at least a distal limb portion of each limb is resiliently deformable into a delivery shape but when not deformed into the delivery shape is configured to cooperatively form with the contralateral limb a loop that can be placed circumferentially around the portion of the target structure in order to locate the encircling implant around the portion of the target structure;
   wherein the encircling implant forms a loop that extends from adjacent the delivery catheter, along a length of the first delivery limb to the distal end of the first delivery limb, across the articulation region to the distal end of the second delivery limb, and along a length of the second delivery limb back to adjacent the delivery catheter; and
   wherein the encircling implant is tubular and the first and second delivery limbs extend within a lumen of the encircling implant during delivery.

2. The system of claim 1, wherein the distal limb portions are cooperatively biased to assume a loop shape and sized substantially complementary to the portion of the target structure around which the loop is to be circumferentially placed.

3. The system of claim 1, wherein the target structure comprises a base portion connected to the body and a free portion over and around which the loop can be passed.

4. The system of claim 1, wherein the target structure comprises a heart or atrial appendage, a cecal appendix, a gallbladder, a neoplasm, a uterus, a hemorrhoid, an uvula, an aneurysm, a transected blood vessel or other transected, folded or looped lumen, an intraocular crystalline lens or implanted intraocular lens or lens haptic, a urinary bladder, a kidney, a prostate or a foreign body.

5. The system of claim 1, wherein the first and second delivery limbs extend alongside a looped portion of a suture within the lumen of the encircling implant during delivery of the encircling implant around the target structure, and with the first and second delivery limbs retracted from the lumen of the encircling implant the looped portion of the suture can be reduced in circumference to tighten the encircling implant around the target structure.

6. The system of claim 1, wherein the first and second limbs are separate and proximal limb portions of the first and second delivery limbs are substantially parallel to one another in the delivery shape, and the distal limb portions are substantially parallel to one another in the delivery shape.

7. The system of claim 6, wherein the proximal and distal limb portions are constrainable into the delivery shape by a lumen within the flexible delivery catheter through which the encircling implant is to be delivered to the target structure in the body, wherein the delivery catheter comprises a distal end for initial introduction into the body and a proximal end for controlling the delivery catheter.

8. The system of claim 7, wherein the proximal limb portions are flexible to conform to the shape of the lumen within the flexible delivery catheter with the proximal limb portions parallel to one another, and the proximal limb portions are sufficiently rigid to maintain a substantially parallel relationship when only a distal portion of the proximal limb portions extends from the lumen, and the proximal limb portions are connected together in at least one location to rotationally constrain the proximal limb portions with respect to each other.

9. The system of claim 1, wherein the first and second delivery limbs are capable of being withdrawn from the encircling implant and from the body once the encircling implant is delivered around the target structure.

10. The system of claim 1, wherein the loop is substantially circular or cordiform and each distal limb portion forms a substantially semi-lunar or semi-cordiform shape joined at the articulation tip.

11. The system of claim 1, wherein the loop extends at a predetermined angle with respect to a longitudinal axis of the delivery catheter.

12. The system of claim 1, wherein the loop folds back toward proximal limb portions.

13. The system of claim 1, wherein the flexible distal limb portions of the first and second delivery limbs cooperatively form geometric shapes that are substantially co-planar or not-coplanar when the flexible distal limb portions form the loop.

14. The system of claim 1, wherein the delivery limbs are removable from their positions within the continuous encircling implant to leave the encircling implant in place around the target structure after the delivery limbs are removed from the encircling implant, and the encircling implant can be tightened after placement around the target structure to circumferentially compress the target structure.

15. A method of using the system of claim 1 to deliver the encircling implant around the target structure in the body through the delivery catheter having a proximal control end and a distal end, the method comprising:

advancing the first and second delivery limbs through the lumen of the delivery catheter with the distal articulation tip leading and with the first and second delivery limbs substantially conforming to a shape of the lumen of the delivery catheter; and further advancing the first and second delivery limbs until the distal limb portions emerge from the lumen at the distal end of the delivery catheter and form the loop while at least a portion of the delivery limbs or a proximal guide member attached to the delivery limbs is retained within the delivery catheter.

16. A system for delivering a continuous flexible encircling implant around a portion of a target structure in a subject's body, the device comprising:

the continuous flexible encircling implant;

a flexible delivery catheter having a lumen, a proximal end for controlling the catheter and a distal delivery end for introduction into the body; and a guide comprising first and second delivery limbs maintained in an articulating relationship at a distal articulation tip by the continuous flexible encircling implant, wherein the encircling implant extends over the first and second delivery limbs and bridges a gap between distal ends of the first and second delivery limbs to form the articulation tip, wherein at least distal portions of the first and second delivery limbs are resiliently deformable into a delivery shape to extend along the longitudinal axis of the delivery catheter, but resiliently assume a loop shape cooperatively formed by the two distal limb portions when not deformed into the delivery shape, and the loop shape has a size and shape substantially complementary to a feature of the target structure such that the distal limb portions cause the encircling implant to assume a loop for placement of the encircling implant around the target structure, wherein the encircling implant forms a loop that extends from adjacent the distal delivery end of the catheter, along a length of the first delivery limb to the distal end of the first delivery limb, across the gap to the distal end of the second delivery limb, and along a length of the second delivery limb back to adjacent the distal delivery end of the catheter; and wherein the encircling implant comprises a tubular implant and the distal portions of the delivery limbs extend through a lumen of the tubular implant.

17. The system of claim 16, wherein at least the distal limb portions comprise a superelastic or shape-memory material.

18. The system of claim 16, wherein the distal limb portions in the delivery shape deflect toward the delivery catheter as the distal limb portions emerge from the distal delivery end of the delivery catheter.

19. The system of claim 16, wherein an orientation of the loop with respect to the delivery catheter is controllable by moving one or both of the first and second delivery limbs.

20. The system of claim 16, wherein the distal limb portions are configured to assume a shape and size substantially complementary to a circumference of the target structure around which the loop is to be circumferentially navigated or placed, and the target structure comprises a body organ, neoplasm, or surgically implanted device.

21. The system of claim 16, wherein the target structure comprises a heart, and the distal limb portions are configured to deflect the loop toward the delivery catheter and around the apex of the heart.

22. A method of delivering an encircling implant for placement around a target structure in a body, the method comprising:

advancing delivery limbs of a delivery guide through an elongated delivery catheter, the delivery catheter comprising a lumen, a proximal control end, and a distal end, with an articulated tip of the delivery guide being advanced through the delivery catheter ahead of the delivery limbs, and with the delivery limbs substantially conforming to the shape of the lumen of the delivery catheter;

wherein the delivery limbs are maintained in an articulating relationship at the articulation tip by a continuous flexible encircling implant, wherein the encircling implant extends through or over the delivery limbs and bridges a gap between adjacent ends of the delivery limbs to form the articulation tip; and further advancing the delivery limbs relative to the delivery catheter until distal limb portions of the delivery limbs emerge from the lumen at the distal end of the delivery catheter and resiliently assume a loop shape causing the encircling implant to form a loop that extends along a length of a first of the delivery limbs, across the gap, and along a length of a second of the delivery limbs, while at least a portion of the delivery limbs or a proximal guide member attached to the delivery limbs is retained within the delivery catheter;

wherein a protection device is advanced over the encircling implant into a desired position with respect to the target structure; and wherein the target structure is the heart, and the protection device is advanced over or within the encircling implant to a position on an external wall of the myocardium to bridge a coronary artery and avoid compression of the coronary artery when the encircling implant is tightened around the heart.

23. The method of claim 22, further comprising placing the loop around the target structure to encircle the target structure.

24. The method of claim 23, further comprising individually or cooperatively moving the first and second delivery limbs to adjust an orientation of the loop with respect to the delivery catheter and the target structure.

25. The method of claim 23, further comprising withdrawing the delivery limbs from the encircling implant into the delivery catheter to leave the encircling implant positioned and secured around the target structure, wherein tension is applied to the encircling implant while the delivery limbs are withdrawn to maintain the encircling implant in a desired position until two free ends of the encircling implant are subsequently secured together.

26. The method of claim 25, further comprising tightening the encircling implant around the target structure.

27. The method of claim 25, further comprising withdrawing the delivery catheter from the body.

28. The method of claim 22, further comprising inserting the distal end of the delivery catheter percutaneously through an introducer sheath into the body and advancing the distal end of the delivery catheter to the target structure within the body, wherein the delivery catheter is advanced intravascularly through the inferior vena cava until the distal end of the delivery catheter penetrates a wall of the heart, then advancing the delivery limbs out of the distal end of the delivery catheter until the distal delivery limbs form the looped shape.

29. The method of claim 28, wherein the loop forms a shape substantially conforming to a circumference of the heart, and the loop assumes a pre-configured angle with respect to the proximal portions of the delivery limbs, and the loop is advanced around the apex of the heart until the loop encircles the heart, then the delivery limbs are withdrawn proximally into the delivery catheter to leave the encircling implant which encircles the heart, and the encircling implant is tightened by exerting tension on terminal ends of the encircling implant or by tightening a suture passing through the implant, to improve a function of a heart valve within the heart.

30. The method of claim 29, wherein
(a) the distal end of the delivery catheter penetrates the heart through an atrial appendage, and the loop substantially conforms to a circumference of a targeted atrial appendage of the heart, and the loop is advanced around the atrial appendage until the loop encircles the targeted atrial appendage, then the delivery limbs are withdrawn proximally into the delivery catheter to expose the encircling implant which encircles the targeted atrial appendage and the encircling implant is tightened by exerting tension on terminal ends of the encircling implant to exclude the targeted atrial appendage; or
(b) the distal end of the delivery catheter approaches the heart by a trans-thoracic or sub-xiphoid path and the loop is advanced around the atrial appendage until the loop encircles the atrial appendage, then the delivery limbs are withdrawn proximally into the delivery catheter to expose the encircling implant which encircles the atrial appendage and the encircling implant is tightened by exerting tension on terminal ends of the encircling implant to tighten the encircling implant and exclude the atrial appendage.

31. The method of claim 22 wherein the distal end of the delivery catheter is inserted intraluminally into a body lumen and advanced to the target structure.

32. The method of claim 22 wherein the distal end of the delivery catheter is inserted percutaneously into the body and advanced to the target structure.

33. The method of claim 32, wherein the distal end of the delivery catheter is inserted percutaneously into a body cavity.

34. The method of claim 22, wherein a compression device is advanced over the encircling implant to a position on the external wall of the myocardium to exert pressure on the external wall and change a shape and function of a valve of the heart.

35. The method of claim 34, wherein the valve is the mitral or tricuspid valve.

36. The method of claim 22, wherein the target structure is the right ventricular outflow tract.

* * * * *